United States Patent
Ketelson et al.

(10) Patent No.: US 12,102,559 B2
(45) Date of Patent: *Oct. 1, 2024

(54) DISSOLVABLE POLYMERIC EYE INSERTS AND METHOD OF USING SAME

(71) Applicant: ALCON INC., Fribourg (CH)

(72) Inventors: Howard Allen Ketelson, Dallas, TX (US); Rekha Rangarajan, Fort Worth, TX (US); Walter R Laredo, Fort Worth, TX (US); Stephen John Collins, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 625 days.

This patent is subject to a terminal disclaimer.

(21) Appl. No.: 16/864,894

(22) Filed: May 1, 2020

(65) Prior Publication Data

US 2020/0345544 A1 Nov. 5, 2020

Related U.S. Application Data

(60) Provisional application No. 62/927,885, filed on Oct. 30, 2019, provisional application No. 62/841,901, filed on May 2, 2019.

(51) Int. Cl.
| | | |
|---|---|---|
| *A61F 9/00* | (2006.01) |
| *A61K 9/00* | (2006.01) |
| *A61K 47/10* | (2017.01) |
| *A61K 47/14* | (2017.01) |
| *A61K 47/22* | (2006.01) |
| *A61K 47/36* | (2006.01) |

(52) U.S. Cl.
CPC .......... *A61F 9/0017* (2013.01); *A61K 9/0051* (2013.01); *A61K 47/10* (2013.01); *A61K 47/14* (2013.01); *A61K 47/22* (2013.01); *A61K 47/36* (2013.01); *A61K 2121/00* (2013.01)

(58) Field of Classification Search
None
See application file for complete search history.

(56) References Cited

U.S. PATENT DOCUMENTS

| | | |
|---|---|---|
| 4,730,013 A | 3/1988 | Bondi |
| 2006/0257450 A1 | 11/2006 | Mudumba et al. |
| 2007/0148283 A1 | 6/2007 | Harvey et al. |
| 2008/0193407 A1 | 8/2008 | Chowhan |
| 2013/0172357 A1 | 7/2013 | Horn |
| 2013/0244978 A1* | 9/2013 | Matsumura ............ A61K 47/36 514/723 |
| 2013/0296264 A1 | 11/2013 | Davis |
| 2014/0107025 A1 | 4/2014 | Wirostko |
| 2015/0157563 A1 | 6/2015 | Wirostko |
| 2017/0119885 A1 | 5/2017 | Ellis et al. |
| 2017/0296483 A1 | 10/2017 | Barman et al. |

FOREIGN PATENT DOCUMENTS

| | | |
|---|---|---|
| EP | 0077261 A2 | 4/1983 |
| JP | S5875547 A | 5/1983 |
| JP | 2010518116 A | 5/2010 |
| WO | 9640005 A1 | 12/1996 |
| WO | 2012112636 A1 | 8/2012 |
| WO | 2014204357 A2 | 12/2014 |
| WO | 2015193677 A1 | 12/2015 |

OTHER PUBLICATIONS

Petricek, I., et al., Expert Opinion on Pharmacotherapy 9(8): 1431-1436 (2008). (Year: 2008).*
Moon Sang-Woong et al. "The Impact of Artificial Tears Containing Hydroxypropyl Guar on Mucous Layer" Cornea,2010, 29(12):1430-5, c. 1431-1433, fig.4.
Bloomfield, Stephen E., et al., "Soluble Artificial Tear Inserts", Archives of Ophthalmology 95, (1977), 247-250.
Nguyen, Theresa, and Robert Latkany, "Review of hydroxypropyl cellulose ophthalmic inserts for treatment of dry eye", Clinical Ophthalmology, 5, (2011), 588-589.
Rangarajan, Rekha, et al., "Effects of a Hyaluronic Acid/Hydroxypropyl Guar Artificial Tear Solution on Protection, Recovery, and Lubricity in Models of Corneal Epithelium", Journal of Ocular Pharmacology and Therapeutics, 31/8, (2015), 491-497.
Karthikeyan, MB et al., Asian J. Pharmacol; Oct.-Dec. 2008; 192-200.
Koffler B, et al., Eye Contact Lens; 2010; 36:170-176.
Luchs, J, et al., Cornea, 2010; 29:1417-1427.
McDonald M, et al., Trans Am Ophthalmol. Soc., 2009; 107:214-221.
Paugh et al., Optom Vis Sci. Aug. 2008; 85(8):725-731.
Pescina S et al., Drug Dev Ind Pharm; 2017:1520-5762.
Saettone M F et al.: "Evaluation of muco-adhesive properties and in vivo activity of ophthalmic vehicles based on hyaluronic acid", International Journal of Pharmaceutics, Elsevier, NL, vol. 51, No. 3, May 1, 1989, pp. 203-212.
Swanson, M., J. Am. Optom.Assoc., 1998; 10:649-655.
Thakral et al.: "Formulation and In Vitro-In Vivo Correlation of Timolol Maleate Ocular Insert", Indonesian Journal of Clinical Pharmacy, vol. 4, No. 4, Dec. 1, 2015, pp. 281-288.
Wander A, and Koffler B, Ocul Surf. Jul. 2009;7(3):154-162.
Xu et al.: "Effect of menthol on ocular drug delivery", Graefe's Archive for Clinical and Experimental Ophthlamology; Incorporating German Journal of Ophthalmology, Springer, Bwerline, DE, vol. 249, No. 10, May 20, 2011, pp. 1503-1510.
Renato Ambrosio Jr, et al., Artificial Tears, Dry Eye Practical Approach, Springer, p. 47, Jan. 1, 2015.

* cited by examiner

*Primary Examiner* — David J Blanchard
*Assistant Examiner* — Daniel F Coughlin
(74) *Attorney, Agent, or Firm* — Sheng-Hsin Hu

(57) ABSTRACT

Polymeric eye inserts are provided that may be dissolvable when placed in the cul-de-sac of the eye. These inserts may contain one or more polymers as well as a softener/plasticizer so that, when inserted into the eye, they may absorb tears, and dissolve and slowly release lubricant into the tear film to lubricate and protect the ocular surface for an extended duration of time. Increased retention time on the ocular surface for longer lasting relief may reduce dosing frequency and patient burden typically associated with topical drop usage. These polymeric eye inserts also may include one or more pharmaceutically active agents.

12 Claims, 29 Drawing Sheets

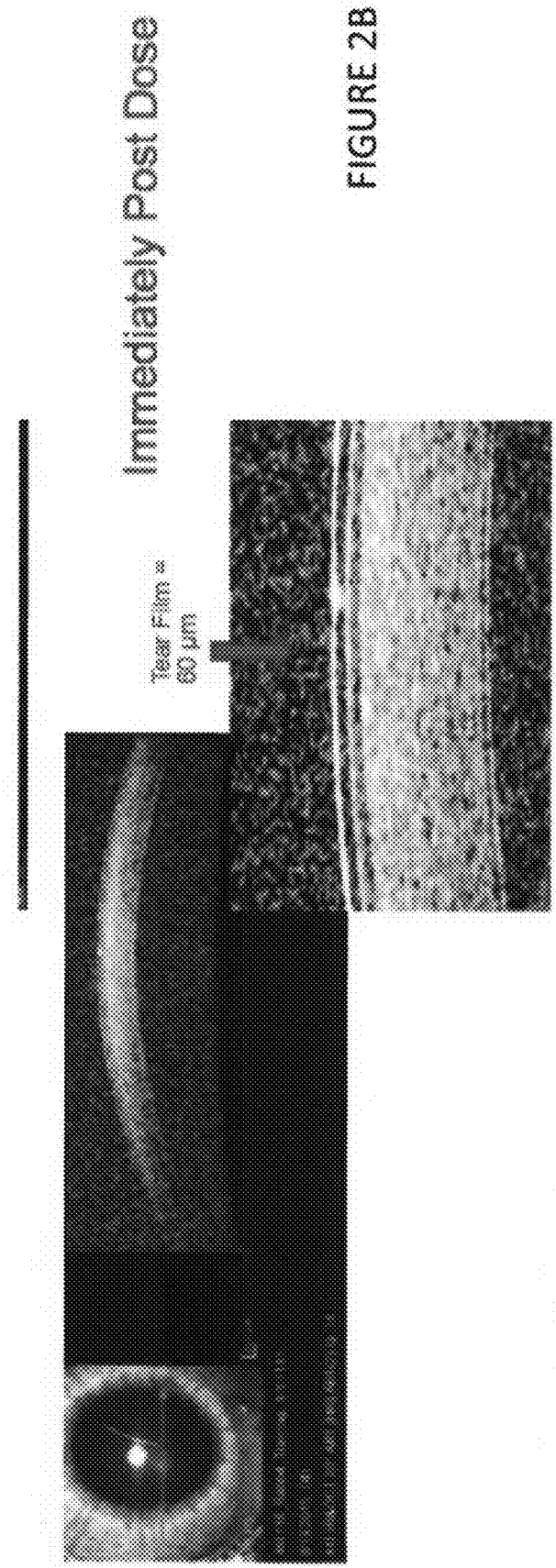

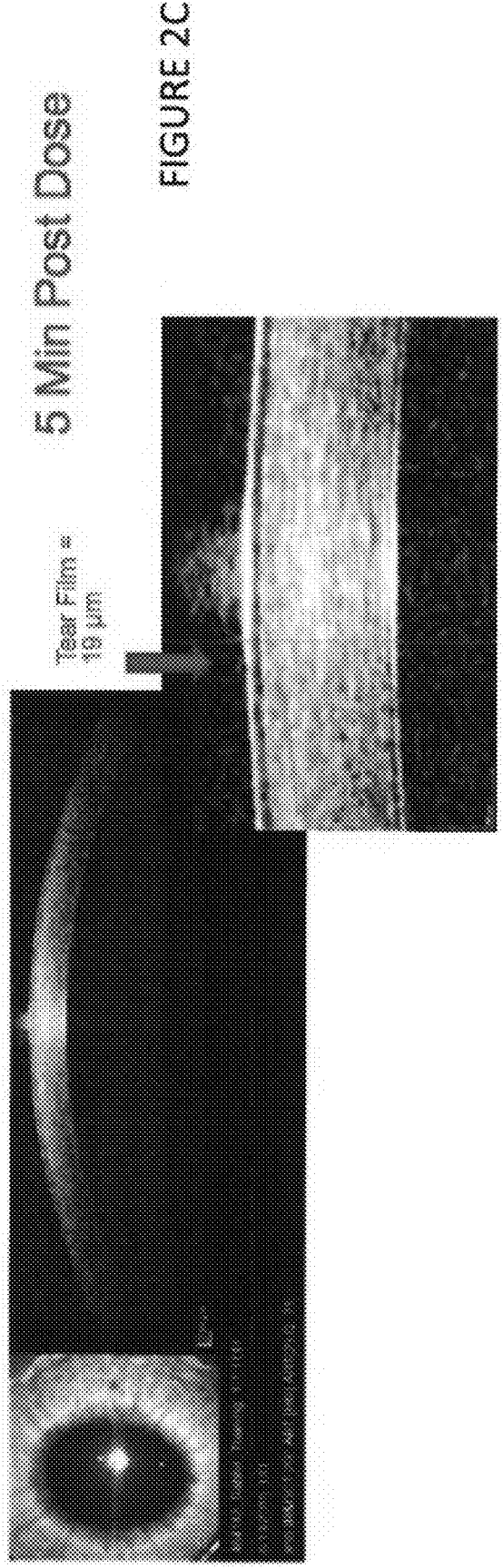

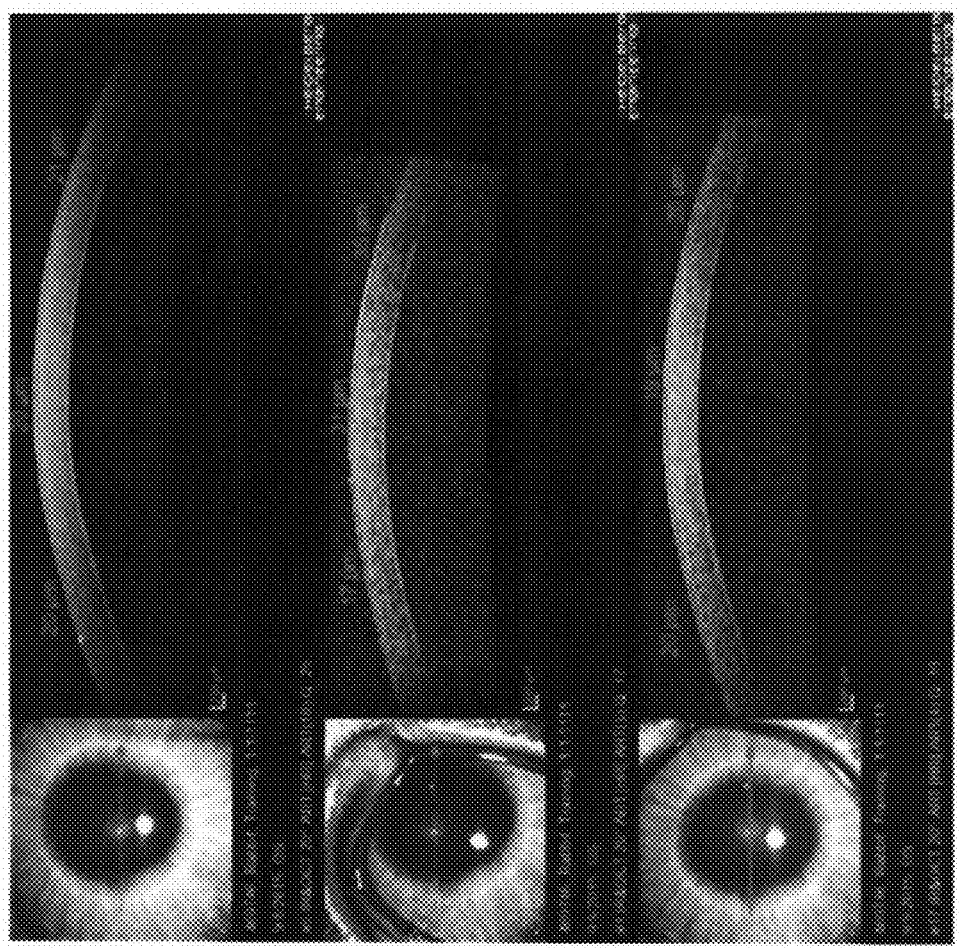
FIGURE 3A  Pre-Dose
FIGURE 3B  Immediately Post Dose
FIGURE 3C  15 Min Post Dose

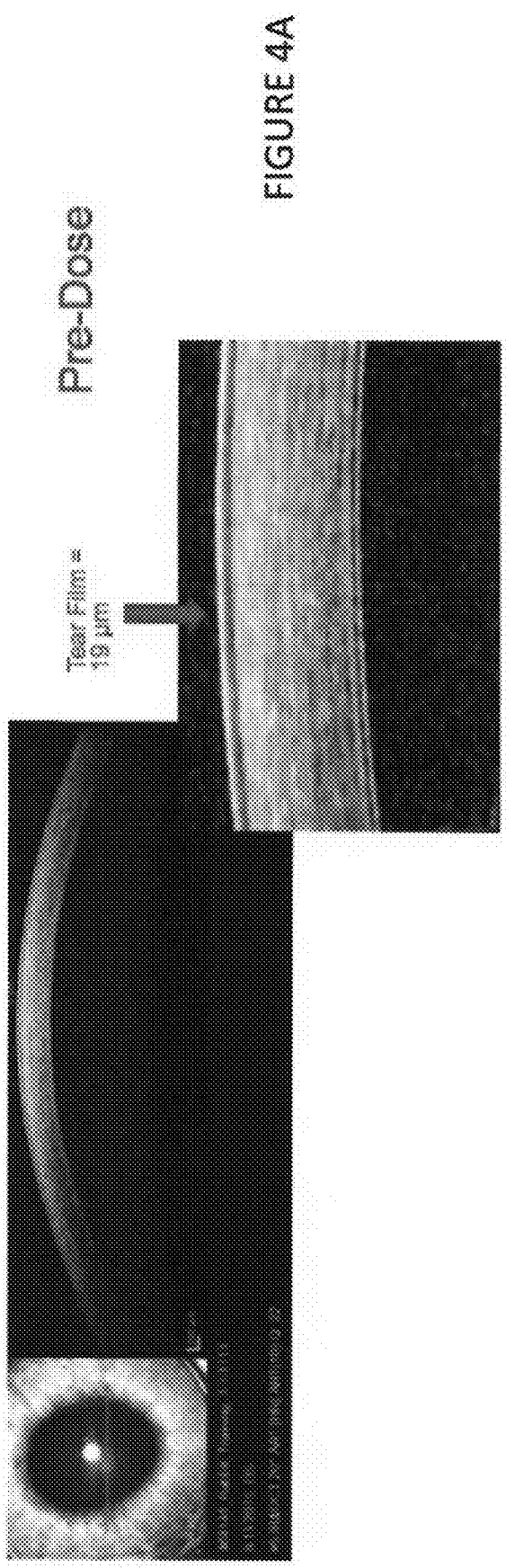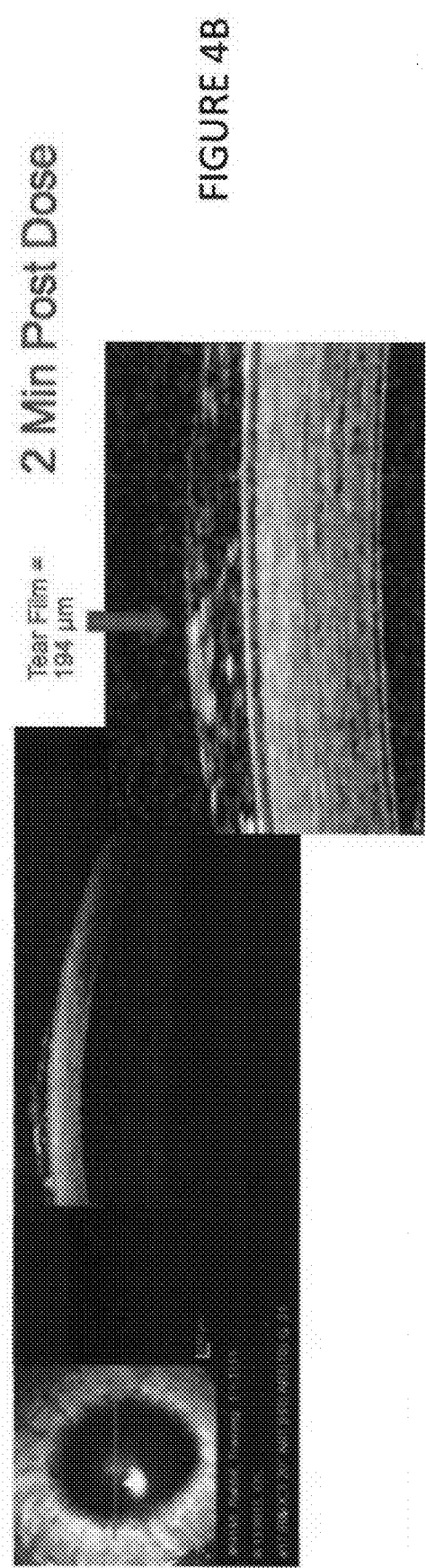
FIGURE 4A Pre-Dose
FIGURE 4B 2 Min Post Dose

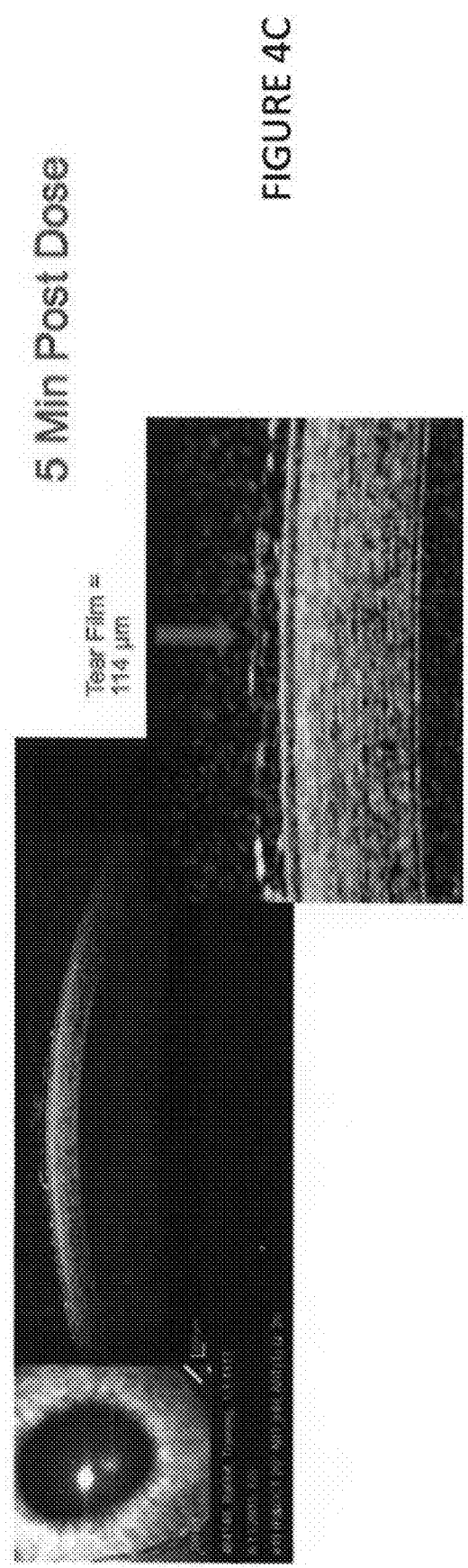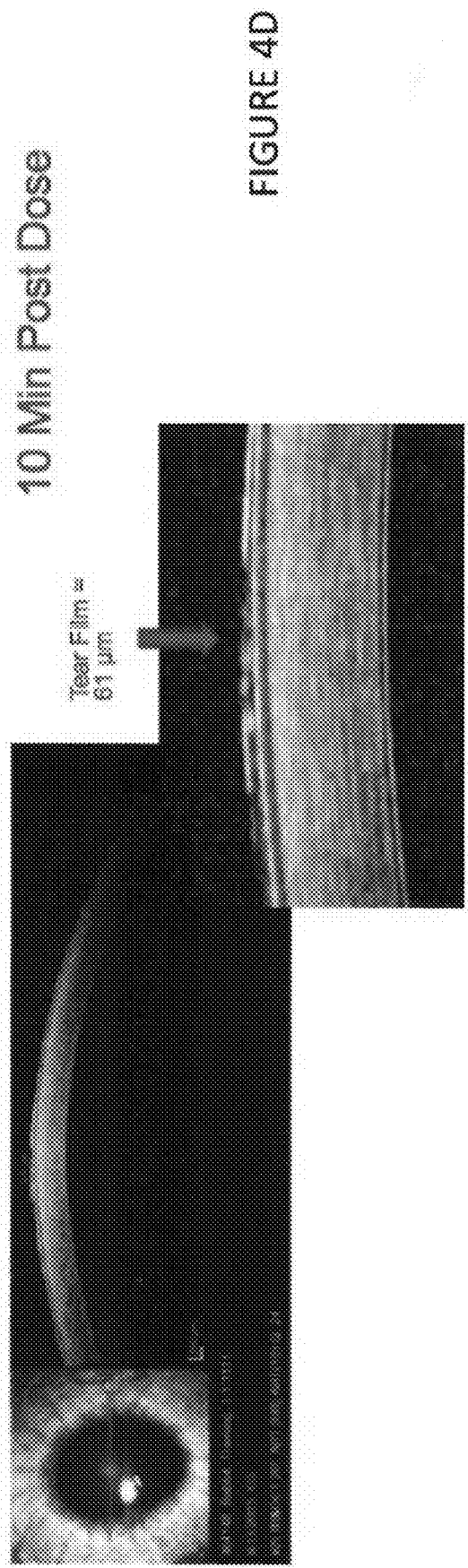

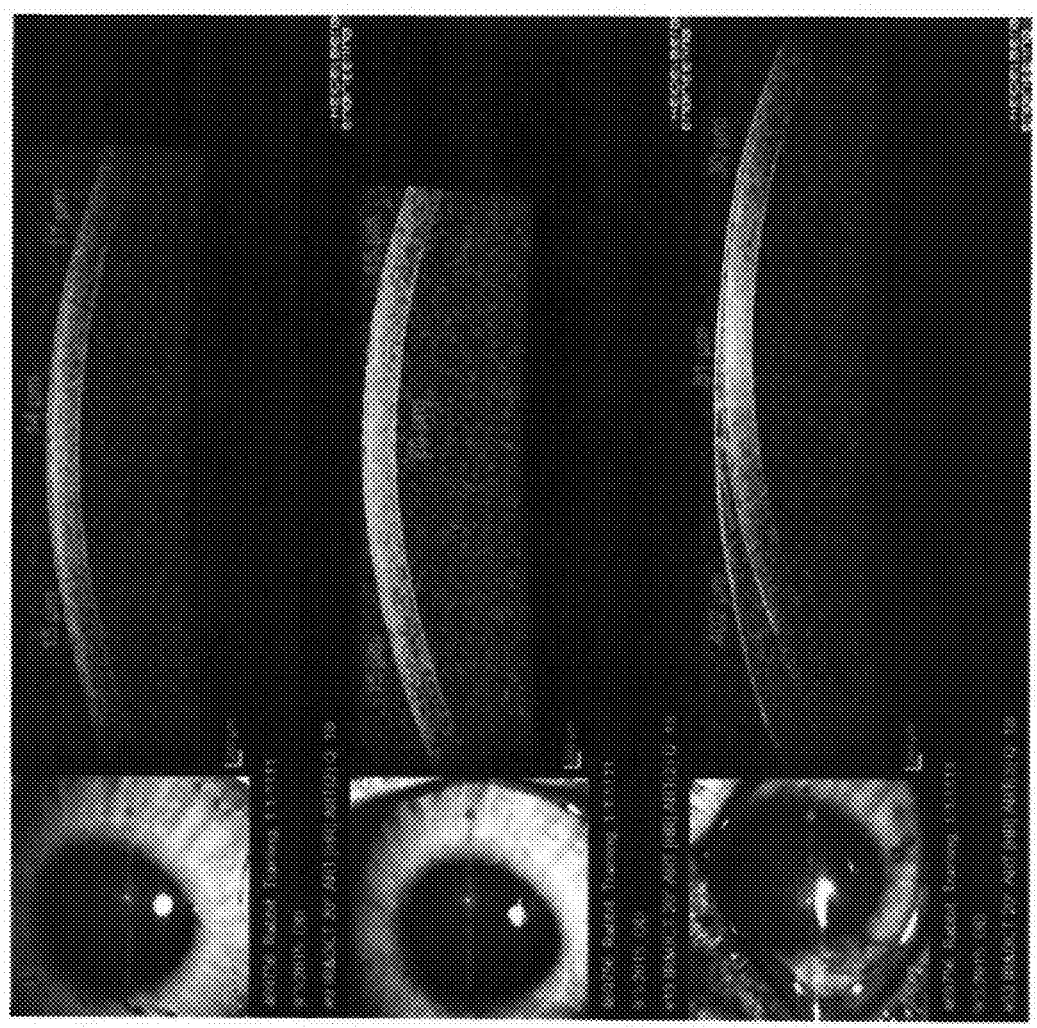
FIGURE 5A Pre-Dose
FIGURE 5B 15 Min Post Dose
FIGURE 5C 30 Min Post Dose

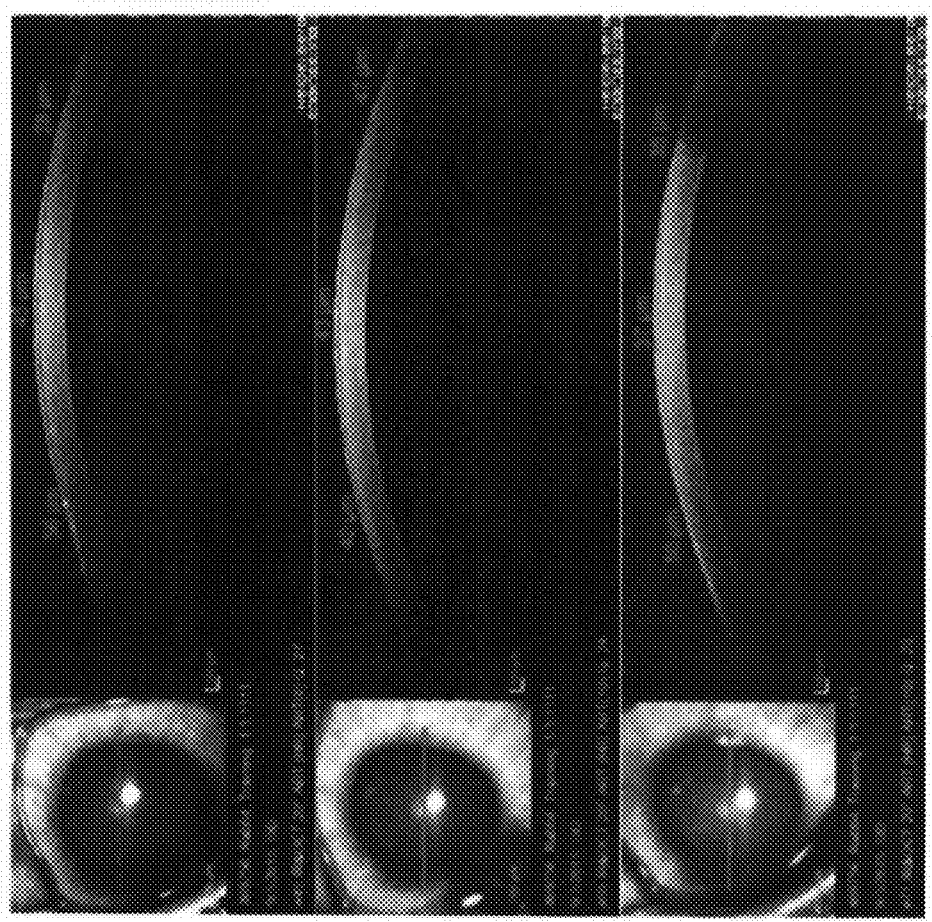
FIGURE 5D  45 Min Post Dose
FIGURE 5E  1 Hr Post Dose
FIGURE 5F  1 Hr 15 Min Post Dose

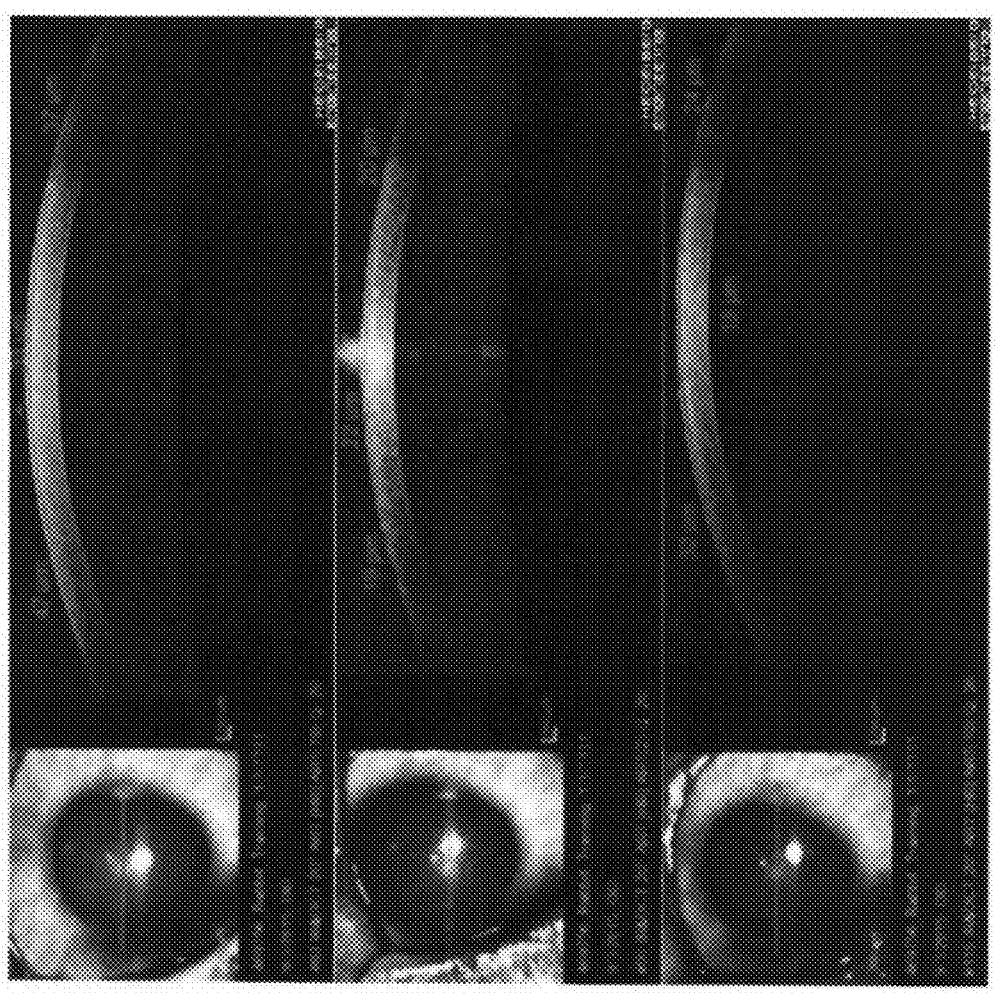
FIGURE 5G  1 Hr 30 Min Post Dose
FIGURE 5H  1 Hr 45 Min Post Dose
FIGURE 5I  2 Hr Post Dose

FIGURE 10A
Naming Convention:
P1-1_8-4_2
P1-1 = Revision Number
8-4 = 8 mm x 4 mm size
2 = 2 mm donut width
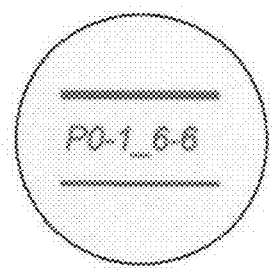
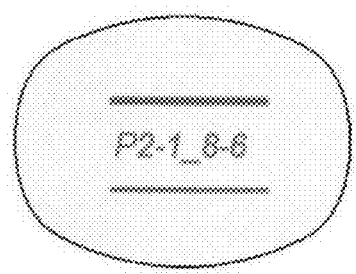
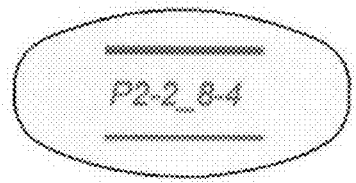
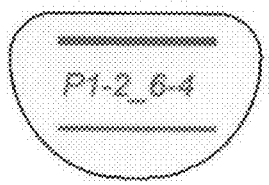
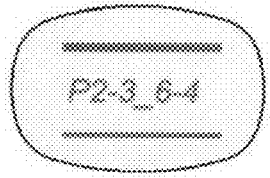

DISSOLVABLE POLYMERIC EYE INSERTS AND METHOD OF USING SAME

FIELD OF THE DISCLOSURE

The present disclosure generally relates to polymeric eye insert technology, and more particularly to dissolvable polymeric eye inserts that release lubricants and drugs into the eye (including, but not limited to the anterior and posterior segments) for an extended duration of time compared to topical drop dosage forms.

BACKGROUND

Many ophthalmic formulations comprise compounds that provide lubricity and other desirable properties. When these formulations are instilled in the eye, the properties of such compounds can prevent undesirable problems such as bioadhesion and the formation of friction-induced tissue damage, as well as encourage the natural healing and restoration of previously damaged tissues.

Compliance with administration of topically applied ophthalmic formulations such as liquids, ointments, gels, sprays is often poor, specifically for the treatment of dry eye, allergy, infection and slowly progressing diseases, such as glaucoma, requiring multiple applications per day to lubricate and deliver a drug to the eye. Exposure to topically administered aqueous formulations is often driven by the short retention time of the formulation on the ocular surface, which can be less than 25 minutes following instillation. Paugh et al., Optom Vis Sci. 2008 August; 85(8):725-31. Typical aqueous formulations for ocular use may be diluted or washed from the ocular surface within minutes, introduce variability in the usage, or result in less accurate and precise dosages administered to the eye. Accordingly, there is a need to reduce treatment burden and improve compliance.

Ointments and gels, which are highly viscous and usually reside in the eye longer than a liquid can provide for more accurate administration. However, they can also interfere with a patient's vision and may require, at a minimum, dosing 2-3 times per day. For these and other reasons the rate of discontinuation of use can be very high. Swanson, M., J. Am. Optom. Assoc., 2011; 10:649-6.

Inserts, both bioerodible and non-bioerodible, are also available and allow for less frequent administration. Pescina S et al., Drug Dev Ind Pharm; 2017 May 7:1-8; Karthikeyan, MB et al., Asian J. Pharmacol; 2008; October-December 192-200. These inserts, however, require complex and detailed preparation and can be uncomfortable to the patient. An additional problem with non-bioerodible inserts is that they must be removed after use. However, with proper use and adequate patient education, inserts can be an effective and safe treatment choice for dry eye patients.

Hydroxypropyl cellulose ophthalmic inserts such as LACRISERT® (Aton Pharmaceuticals Inc.) have been used for dry eye patients. These inserts are translucent cellulose-based rods measuring 1.27 mm in diameter and 3.5 mm in length. Each of these inserts contains 5 mg of hydroxypropyl cellulose, with no preservatives or other ingredients. The medication is administered by placing a single insert into the inferior cul-de-sac of the eye beneath the base of the tarsus. These inserts are indicated particularly for patients who continue to have dry eye symptoms following an adequate trial therapy with artificial tears. They also are indicated for patients with keratoconjunctivitis sicca, exposure keratitis, decreased corneal sensitivity, and recurrent corneal erosions. Several studies have been performed to evaluate the efficacy of HPC ophthalmic inserts. (Luchs, J, et al., *Cornea*, 2010; 29:1417-1427; Koffler B, et al., *Eye Contact Lens;* 2010; 36:170-176; McDonald M, et al., *Trans Am Ophthalmol. Soc.,* 2009; 107:214-221; Wander A, and Koffler B, *Ocul Surf* 2009 July; 7(3):154-62).

However, there also are challenges in using these types of inserts. For example, LACRISERT® inserts tend to dissolve slowly and can remain in the eye even after 15-20 hours. The rod is hard and inelastic with edges due to rod-shaped design. The slow dissolving properties coupled with the rod hardness and design may lead to side effects including blurred vision, foreign body sensation and/or discomfort, ocular irritation or hyperemia, hypersensitivity, photophobia, eyelid edema, and caking or drying of viscous material on eyelashes. The most common side effect of these hydroxypropyl cellulose ophthalmic inserts is blurred vision due to the long retention time of the insert. Thus, additional approaches are needed to develop polymeric eye inserts that are comfortable and improve patient compliance.

SUMMARY

The invention provides a polymeric eye insert, the insert comprising: one or more mucoadhesive polymers that are biocompatible with the ocular surface and tear film of the eye; and wherein upon insertion of the polymeric eye insert in the cul-de-sac of the eye, the thickness of the tear film increases for at least 30 minutes post-insertion. The invention also provides a method for of treating an ocular disorder, which comprises applying the polymeric eye insert of the insert according to embodiments of the present disclosure to the cul-de-sac of the eye.

The present invention is partly based on the finding that problems of tending to dissolve slowly and remaining in the eye even after 15-20 hours in using commercially available ophthalmic inserts such as LACRISERT® inserts. The problem may be solved through using a polymeric eye insert according to embodiments of the present disclosure which is small enough to fit into the cul-de-sac of the eye and be rapidly wetted so that there is little or no irritation upon insertion and the insert is also large enough to allow for dissolution over anywhere from approximately 30-120 minutes to allow for release of the lubricant(s) and/or pharmaceutically active agents to occur. The insert also has a thickness that is relatively comfortable for the user. A preferred thickness is between 50-250 microns, and a most preferred thickness is between 70-150 microns. The target thickness is 90 microns for films dissolving in less than 2 hours

BRIEF DESCRIPTION OF THE DRAWINGS

For a more complete understanding of this disclosure, reference is now made to the following description, taken in conjunction with the accompanying drawings, in which:

FIGS. 2A-2C depict tear film measurements for SYSTANE® ULTRA eye drops pre-dose (FIG. 2A), immediately post-dose (FIG. 2B) and 5 minutes post-dose (FIG. 2C);

FIGS. 3A-3C depict tear film measurements for GENTEAL® gel drops pre-dose (FIG. 3A), immediately post-dose (FIG. 3B) and 5 minutes post-dose (FIG. 3C);

FIGS. 4A-4E depict tear film measurements for PRO-VISC® injectable pre-dose (FIG. 4A), immediately post-dose (FIG. 4B), 5 minutes post-dose (FIG. 4C), 10 minutes post-dose (FIG. 4D) and 20 minutes post-dose (FIG. 4E);

FIGS. 5A-5I reflect tear film measurements associated with insertion of a polymeric eye insert according to embodiments of the present disclosure;

FIGS. 10A-10C illustrate various polymeric eye insert shapes and characteristics according to embodiments of the present disclosure.

DETAILED DESCRIPTION

Figure 1:
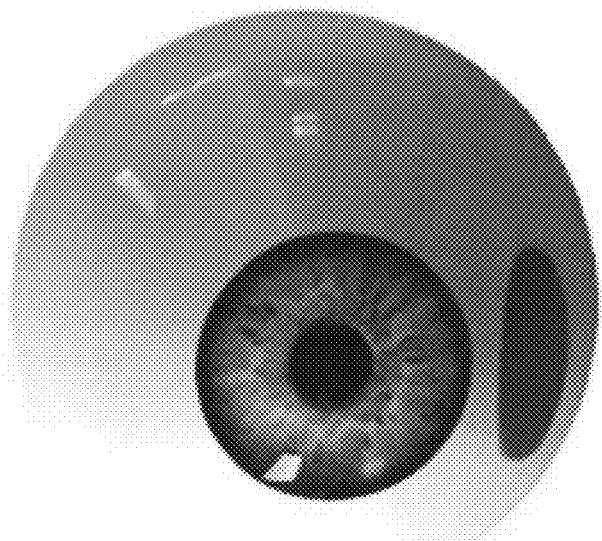
FIG. 1 depicts placement of a polymeric eye insert according to embodiments of the present disclosure.

Embodiments of the present disclosure provide a polymeric eye insert comprising an ocular lubricant containing one or more polymers. In an embodiment of the present disclosure, a polymeric eye insert may be comprised of hyaluronic acid, hydroxypropyl guar (HP guar), and a plasticizer, such as polyethylene glycol (PEG); however, other polymers and plasticizers/softeners may be used without departing from the present disclosure, as described herein. An insert according to embodiments of the present disclosure may be inserted in the lower eye lid (also known as the cul-de-sac) of the eye, and upon insertion, the insert may rapidly absorb tears and dissolve to release the ocular lubricant into the tear film to lubricate and protect the ocular surface for an extended duration superior to previously known topical ophthalmic compositions. Pharmaceutically active agents also may be incorporated into polymeric eye inserts according to embodiments of the present disclosure. Insertion of a polymeric eye insert according to embodiments of the present disclosure may provide relief to the patient from symptoms of dry eye as well as other eye conditions.

The biomaterial for forming a polymeric eye insert according to embodiments of the present disclosure may be comprised of one or more polymers that are biocompatible with the ocular surface and tear film. Polymers that may be used in polymeric eye inserts according to embodiments of the present disclosure include, but are not limited to, hyaluronic acid (in acid or salt form), hydroxypropylmethylcellulose (HPMC), methylcellulose, tamarind seed polysaccharide (TSP), Galactomannans, for examples; guar and derivatives thereof such as hydroxypropyl guar (HP guar), scleroglucan poloxamer, poly(galacturonic) acid, sodium alginate, pectin, xanthan gum, xyloglucan gum, chitosan, sodium carboxymethylcellulose, polyvinyl alcohol, polyvinyl pyrrolidine, carbomer, polyacrylic acid and/or combinations thereof.

The preferred biocompatible polymers are hyaluronic acid, guar and derivatives and/or combinations thereof. Hyaluronic acid is an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. As used herein, the term hyaluronic acid also includes salt forms of hyaluronic acid such as sodium hyaluronate. A preferred hyaluronic acid is sodium hyaluronate. The weight average molecular weight of the hyaluronic acid used in insert of the present invention may vary, but is typically weight average molecular weight of 0.1 to 2.0M Daltons. In one embodiment, the hyaluronic acid has a weight average molecular weight of 0.5 to 1MDaltons. In another embodiment, the hyaluronic acid has a weight average molecular weight of 1.5 to 2.0 M Daltons.

The galactomannans of the present invention may be obtained from numerous sources. Such sources include from fenugreek gum, guar gum, locust bean gum and tara gum. Additionally, the galactomannans may also be obtained by classical synthetic routes or may be obtained by chemical modification of naturally occurring galactomannans. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-.beta.-D-mannopyranosyl units with.alpha.-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethyl-hydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired, Preferred galactomannans of the present invention are guar and hydroxypropyl guar. Hydroxypropyl guar is particularly preferred. The weight average molecular weight of the Hydroxypropyl guar in the insert of the present invention may vary, but is typically 1 to 5M Daltons. In one embodiment, the Hydroxypropyl guar has a weight average molecular weight of 2 to 4MDaltons. In another embodiment, the Hydroxypropyl guar has a weight average molecular weight of 3 to 4 M Daltons.

Polymers used in inserts according to embodiments of the present disclosure should be non-toxic and able to solubilize in eye fluids to ensure that the insert is eventually cleared from the eye, generally over a 60-minute time frame. It should be appreciated that the polymer(s) selected should be mucoadhesive. It also should be appreciated that one or more polymers may be blended according to embodiments of the present disclosure. For example, in an embodiment of the present disclosure, hyaluronic acid (HA) may be blended with tamarind seed polysaccharide (TSP) because TSP has been shown to increase residence time of HA in aggregate blends and the blend has desired film mechanical and lubrication properties. In other embodiments of the present disclosure, as described in further detail below, hyaluronic acid may be combined with HP guar.

In some embodiments, the one or more mucoadhesive polymers are present in an amount of from about 50% to about 99% w/w, about 60% to about 95% w/w, about 70% to about 90% w/w, or about 80% to about 90% w/w by dry weight of the polymeric eye insert. In particular embodiments, the mucoadhesive polymers are present in an amount of about 75%, about 80%, about 85%, about 90%, or about 95% w/w by dry weight of the polymeric eye insert. The overall dry weight or mass of the polymeric eye insert may be in the range of about 1 to about 10 mg, or about 2 to about 8 mg, and in particular embodiments may be from about 2.5 to about 5 mg.

In some embodiments of the present disclosure, a softener and/or plasticizer may be added to the one or more polymers to facilitate fabrication of a softer, malleable delivery system and also provide improved comfort in insertion. A plasticizer may soften the material to provide for desirable dissolution rates. It should be appreciated softeners and/or plasticizers may be low or high-molecular weight compounds, including not limited to, polyethylene glycol (PEG) and derivatives thereof, water, Vitamin E, and triethyl citrate.

In some embodiments, the plasticizer or softener is present in an amount of from about 2% to about 30% w/w, about 5% to about 25% w/w, about 5% to about 20% w/w, or about 5% to about 15% w/w by dry weight of the polymeric eye insert. In particular embodiments, the plasticizer or softener is present in an amount of about 5%, about 7%, about 10%, or 12%, or about 15%, w/w by dry weight of the polymeric eye insert.

In some embodiments, the polymeric eye insert may have a water content of about 1% to about 50% after hydration. In particular embodiments, the polymeric eye insert may have a water content of 30-40%.

Figure 10B:
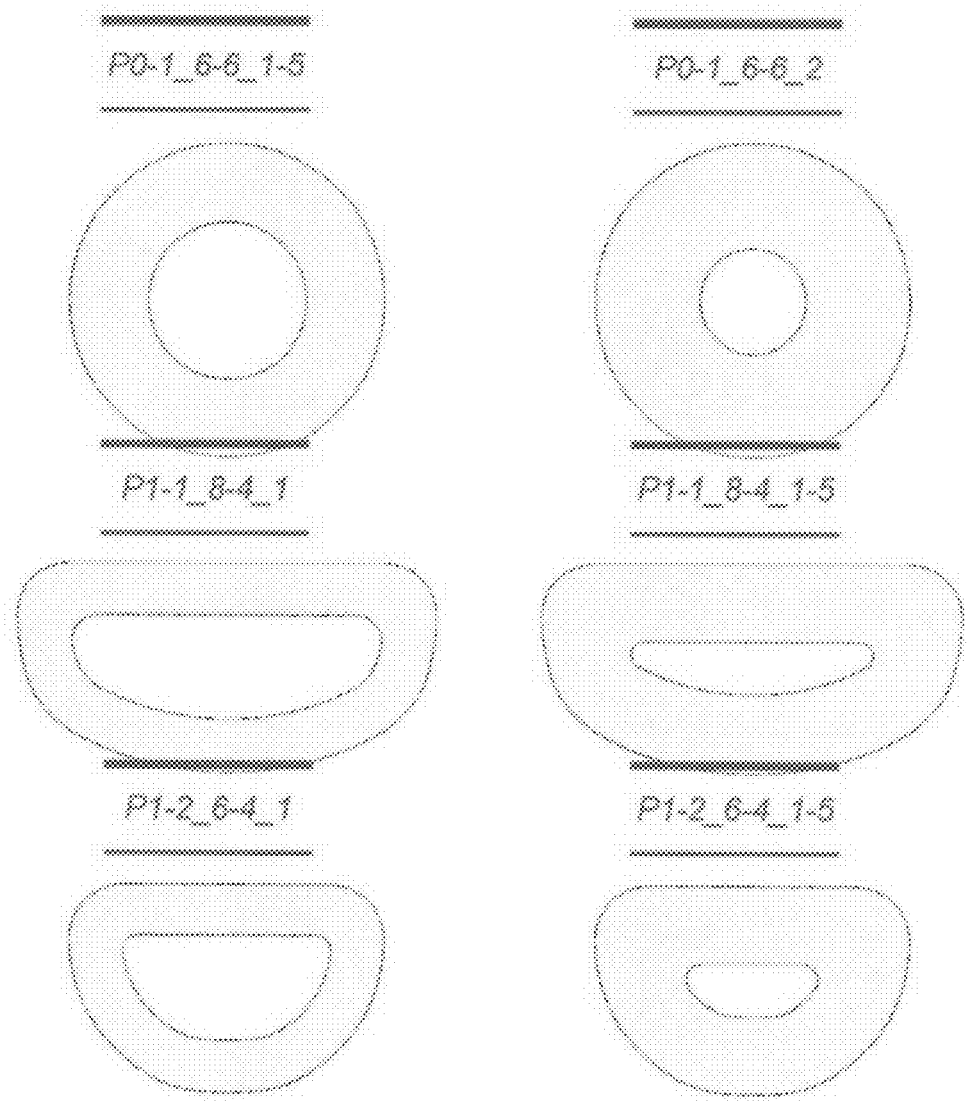
Figure 10C:
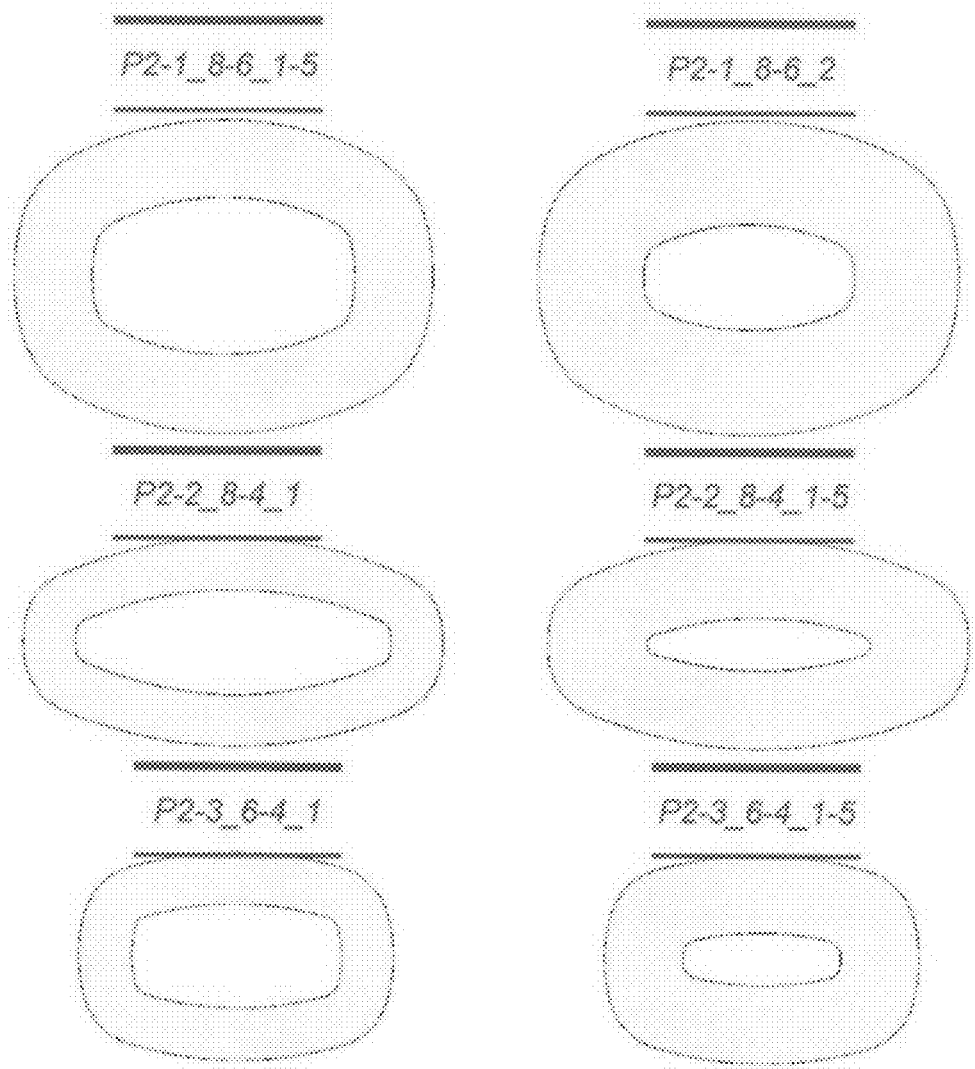

The polymeric eye insert may be of any size or shape suitable for administration to the eye. Exemplary shapes include film, a rod, a sphere, or an irregular shape having a maximum size in any single dimension of 5-6 mm. Additional exemplary shapes are shown in FIGS. 10A-10C.

In some embodiments, the polymeric eye insert has a thickness of about 50-400 µm, about 100-300 µm, about 150-250 µm, or about 200 µm.

In particular embodiments, the polymeric eye insert has a thickness of about 150-250 µm, and a water content of 30 to 50% w/w.

In some embodiments of the present disclosure, the polymeric eye insert does not include an additional pharmaceutically active agent. In other embodiments, the polymeric eye insert may include one or more additional pharmaceutically active agents. In some embodiments, the one or more pharmaceutically active agents may be selected from the group of ocular lubricants, anti-redness relievers such as alpha-2 adrenergic agonists such as brimonidine, apraclonidine etc, sympathomimetic amines such as tetrahydrozoline, naphazoline, TRPM8 agonists such as menthol, menthol analogs, steroids and nonsteroidal anti-inflammatory agents to relieve ocular pain and inflammation, antibiotics, antihistamines such as olopatadine, anti-virals, antibiotics and anti-bacterials for infectious conjunctivitis, anti-muscarinics such as atropine and derivatives thereof for myopia treatment, and glaucoma drug delivery such as prostaglandin and prostaglandin analogs such as travoprost, or therapeutically suitable combinations thereof.

Polymeric eye inserts according to embodiments of the present disclosure may be made using various processing techniques, including but not limited to, compression molding and solution casting. Compression molding may be carried out at temperatures and pressures that do not change the material or lead to significant side reactions. For example, compression molding of partially hydrated polysaccharides may use a compressional force of approximately 5,000-12,000 pounds at approximately 200-300 degrees Celsius for approximately 1-2 minutes. Solution or film casting may be carried out using solvents and/or co-solvents that may provide homogeneous films with little to no defects. The solvent may be removed by air or vacuum drying, resulting in an insert material that may be free from residual solvents. For example, a 1% (w/v) aqueous solution of polymer (or blend) may be cast and then allowed to evaporate. The film may then be cut with an oval-shaped punch of desired size and geometry. While compression molding and solution/film casting have been described, it should be appreciated that other processing techniques may be used without departing from the present disclosure.

In one embodiment, the film casting method used was found to generate reproducible inserts and good structural integrity. In this embodiment, distilled water was placed in a 1L Erlenmeyer flask followed by the addition of the polymer (s). The flask was placed in a sonicator and attached to an overhead mechanical stirrer. The mixture was sonicated and stirred for 60 minutes at 30° C. The speed of the mechanical stirrer was adjusted to 700 rpm and allowed to stir for 60 minutes. The stirring was stopped and the plasticizer (PEG and/or PVP) was added to the flask. This mixture was stirred for 30 minutes under sonication at 700 rpm at 30° C. until a homogeneous, clear solution was obtained. The mechanical stirring was then stopped and the sonication was allowed to continue for an additional 30 minutes in order to remove all bubbles. The Erlenmeyer flask was then removed from the sonicator and left to sit at room temperature for 30 minutes. For the preparation of the films, a petri dish (150 mm diameter×15 mm height) was filled with about 150 g±2 g of the stock solution. The stock solution was subjected to different evaporation techniques evaluation. In a first experiment, a vacuum oven at 50° C. was used. The petri dishes were placed in the oven and the oven was evacuated using a vacuum pump. After 30 hours, the films obtained were yellow in color and some of the films exhibited curved surfaces. The experiments were repeated at 45° C., 40° C., and 35° C., under the same vacuum conditions. All of the experimental conditions above yielded colored films or films with non-uniform weight distribution. It was also observed that the higher the temperature, the darker and more intense the yellow color became. A preferred evaporation technique included evaporation in a chamber equipped with a variable-speed exhaust at room temperature. The airflow, temperature, and humidity were all measured during the evaporation process. The technique described above produced uniform evaporation and films with consistent thickness.

As previously discussed, in vivo studies indicate that traditional topical ophthalmic lubricants do not remain in the eye longer than approximately 25 minutes. However, use of one or more polymers combined with a plasticizer/softener, such as HP guar and hyaluronic acid blended with a plasticizer (such as PEG), may provide flexible films with tunable hydration and dissolution rates for comfortable insertion. While certain embodiments of the present invention are polymeric eye inserts containing a blend of hyaluronic acid, HP guar and PEG, it should be appreciated that other blends may be employed for polymeric eye inserts according to other embodiments of the present disclosure. FIG. 1 depicts placement of an eye insert according to an embodiment of the present invention on the surface of the eye.

The eye inserts of the present disclosure are a platform to deliver lubricants and other pharmaceutically active agents to treat ocular surface symptoms (such as redness, itching and dryness). In some embodiments, the polymeric eye inserts can be used to prolong exposure of pharmaceutically active agents or provide extended drug delivery of pharmaceutically active agents to the eye. Thus, in some embodiments, the present disclosure provides a method of providing extended drug delivery or prolonging exposure of a pharmaceutically active agent to the eye, by administering a polymeric eye insert including the pharmaceutically active agent to a patient in need thereof.

In some embodiments, the present disclosure provides a method of treating or reducing the signs and/or symptoms of dry eye disease (keratoconjunctivitis sicca), comprising administering a polymeric eye insert according to the present disclosure to a patient in need thereof.

The following non-limiting Examples are provided to illustrate embodiments of the invention.

EXAMPLES

Example 1

In an embodiment of the present disclosure, hyaluronate-fluorescein (Creative PegWorks; Chapel Hill, NC), sodium hyaluronate (Novozyme; Franklinton, NC), HP guar, HP guar-fluorescein, PEG 400, and water may be used to form a polymeric eye insert comprising HP guar and sodium hyaluronate; however, it should be appreciated that more or fewer components from different lots and/or distributors may be used to form a polymeric eye insert without departing from the present disclosure.

In order to form this HP guar/sodium hyaluronate insert, approximately 100 mL of water was added to an Erlenmeyer flask that had been autoclaved for approximately 30 minutes. The water was at a temperature of approximately 22 degrees Celsius. The HA component was tagged with fluorescein isothiocyanate (FITC) for tracking in vivo release. FITC-hyaluronic acid (approximately 102.2 mg) was then added to the water while stirring at approximately 23 degrees Celsius at a setting of 500 (1/min) using an IKA® Ret Control-Visc C hotplate/stirrer. Sodium hyaluronate (approximately 354.3 mg) was then added followed by HP guar (454.1 mg) and PEG 400 (approximately 97.2 mg). Additional water (approximately 100 mL) was then added. The mixture was stirred for approximately 20 hours at ambient temperature (approximately 22 degrees Celsius) using a stirring setting of 600 (1/min). The solution was then poured into a sterile polystyrene disposable petri dish (VWR, diameter of 55 mm, height of 15 mm). The petri dish containing the solution was then placed in a Lindberg Blue M convection oven (Thermo Scientific), heated at approximately 35 degrees Celsius, and then dried under high vacuum at approximately 23 degrees Celsius for approximately 1-2 days.

The resulting composition for this embodiment of a polymeric eye insert was as follows: 102.2 mg (approximately 10%) FITC-hyaluronic acid/354.3 mg (approximately 35%) sodium hyaluronate, 454.1 mg (approximately 45%) HP guar, and 97.2 mg (approximately 9%) PEG 400. Discs having a diameter of 6 mm were then punched out for in vivo assessment studies. While a methodology for forming an HP guar/hyaluronic acid insert according to an embodiment of the present disclosure has been described, it should be appreciated that other methodologies may be employed to form these or similar polymeric eye inserts without departing from the present disclosure.

An in vivo tolerability study was performed using single polymeric eye inserts and New Zealand white rabbits. The polymeric eye inserts utilized in this study were composed of 3-7 mm discs containing an HP guar/hyaluronic acid blend using PEG as a plasticizer. The hyaluronic acid component was tagged with fluorescein isothiocyanate (FITC) for tracking in vivo release. This study revealed acceptable tolerability and comfort using a 200 μm thick film with a diameter of 6 mm. An in vivo retention study also was performed using a single film of HP guar/hyaluronic acid/PEG blend (using 5% FITC-hyaluronic acid). The film hydrated in the cul-de-sac of the eye but fragments remained after two hours. However, these fragments may be explained through low frequency and intermittent blinking associated with the rabbit subjects. Results from measuring fluorescence of these polymeric eye inserts are shown in TABLE 1:

TABLE 1

FLUORESCENCE OF THIN FILM INSERTS-TIME POINTS WITH ≥1.5X BASELINE LEVEL

| Film Sample | Minutes Post-Dose | | | | | | | |
|---|---|---|---|---|---|---|---|---|
| | 2 | 10 | 20 | 30 | 45 | 60 | 90 | 120 |
| Film #1 | | X | X | X | X | X | X | |
| Film #2 | | | X | X | X | X | X | |
| Film #3 | | | | | X | X | | |

All of the polymeric eye inserts were very well tolerated with no physical reactions, discharge, squinting, or pawing. Once placed, the insert remained in the eye with very little movement until dissolved. Inserts dissolved during the first 30 minutes after insertion. After one hour, lubricant residue was visible on the corneal surface. After 6 hours, residue was no longer present. It was determined that the 6-mm size was the largest diameter that would fit in the cul-de-sac without infringement over the corneal-scleral limbus. At 7 mm in diameter, the insert crossed the limbus. However, other diameters of inserts may be employed without departing from the present disclosure.

Tests to study polymeric eye inserts according to embodiments of the present disclosure have been performed using a Spectralis HRA-OCT. This is a diagnostic device that integrates SD-OCT with the cSLO fundus imaging. The Anterior Segment Module provided through the Spectralis may allow for imaging of anterior segment structures. SD-OCT imaging is desirable because it does not require a tagged test article, it offers both visual and quantitative properties, it provides direct micrometer measurement of the tear film/polymeric eye insert, and it allows for acquisition of tear film height from four quadrants of the eye in seconds. Through this image, pooling of the polymeric insert in the lower tear meniscus can be viewed.

Example 2

A variety of polymer inserts were prepared by film casting in order to assess the compatibility of the polymers to make clear and/or reasonably transparent insert films. The following polymer formulations were prepared and evaluated using various concentration ratios of each specified polymer: HA/PEG, HA/PVP/PEG, HA/PVP, HA/HP-Guar/PEG, HP-Guar/PVP/PEG, HA/HP-Guar/PVP/PEG, HA/HP-Guar/PAA/PEG, HA/HP-Guar/HPMC/PEG. A description of the characterization methods of the insert films is provided below.

1. Morphology

The surface morphology of the insert films was tested using the appropriate microscope. The texture and the transparency of the insert films were investigated and the observations were recorded. If the film surface was found to be clear and transparent it was noted. If undissolved particulate or haziness were observed this was also noted.

2. Thickness Uniformity

Four films were sampled and their thicknesses were evaluated by cutting insert disks with 6 mm diameters. The thicknesses of the disks were measured. The positions of the disk cutting were selected randomly, in the middle and near the edges of each film. The disks thicknesses were measured using a Mitutoyo digital caliper. The mean and the standard deviation of 12 disks were calculated for each film.

3. Weight Uniformity

In order to determine the weight uniformity, four different films were selected and 12 disks with 6 mm diameters were cut. The positions of the disks cut were selected randomly on the original films. The weight of each disk was determined using a high accuracy Sartorius balance. The weight of each individual disk was measured and the average weight of 12 disks was determined for each film. The standard deviation for the 12 data points was calculated and recorded.

4. Percentage Moisture Absorption

For the percentage moisture absorption test, four circular films with 150 mm diameters were prepared. From each film, four circular disks with 20 mm diameters were cut. The four disks were placed inside a chamber containing a 100 ml saturated solution of aluminum chloride. The chamber was closed tightly for 72 hours. During this time, the disk surface appearance stayed clear. The disks were carefully removed from the chamber and the weight of each disk was measured.

The percentage moisture absorption of each disk was calculated according to the following formula:

$$\% MA = ((\text{Final weight} - \text{initial weight})/\text{initial weight}) \times 100$$

The average percentage moisture absorption for 12 disks cut from four different films was recorded.

5. Percentage Moisture Loss

The same films produced for percentage moisture absorption were used for the percentage moisture loss measurements. Four disks above were placed in a desiccator containing anhydrous calcium chloride for 72 hours. The disks were then removed from the desiccator and their weights were determined. The percentage moisture loss for each film was calculated using the equation below:

$$\% ML = ((\text{initial weight} - \text{final weight})/\text{final weight}) \times 100$$

The average moisture loss for the 12 disks cut from four different films was recorded.

6. Folding Endurance

Four large, circular films with diameters of 150 mm were prepared. Four square films with 4 cm×4 cm dimensions were prepared from each film. The film strips were repeatedly folded at the same place until the films broke or visibly cracked. The number of times the films could be folded at the same place without breaking gave the value of folding endurance. The data was collected and the average results were recorded. The average folding endurance of 16 square strips cut from the four different films was determined.

7. Dissolution Time and pH of the Solution

Four circular disks with 6 mm diameters were cut from the main circular films with 150 mm diameters. The films were placed in a vial with 2 ml of DI water and the time required for complete dissolution was recorded. The average dissolution time and the standard deviation for each group were recorded.

8. Tensile Strength, Modulus, Displacement, and Percent Elongation

Four film strips with 4 cm×2 cm dimensions were used for each data point measurement. All films were inspected for air bubbles and physical imperfections. The film strips were held between two clamps positioned at 3 cm distances during the measurement. The cell load used was 5 Kilograms. The strips were pulled by the top clamp at a rate of 10 cm/min. The average tensile strength, modulus, and percent elongation were measured and reported. Formulations used to prepare test films are provided below with the polymer compositions and testing data. The TABLE 2 results indicate that the presence of 5% PVP in the HA/PEG formulation improved the flexibility and elasticity of the film. As shown in TABLE 3, the presence of 30% PVP and 30% HP guar also provided a film of relatively good elasticity and flexibility. The presence of carbopol in the tested formulations resulted in brittle films as shown by the data in TABLE 4. 200 ppm of menthol led to faster dissolution rates and produced stiff films as shown in TABLE 5. The films with <200 ppm menthol (such as 150 ppm) were improved with similar modulus and % elongation to same films without menthol added.

TABLE 2

HA/PVP AND PEG COMBINATIONS

| Formulation | Dissolution time (min) | Surface pH | Modulus (MPa) | Tear strength (MPa) | % elongation | Description |
|---|---|---|---|---|---|---|
| HA (45.4%): PVP (45.4%): PEG (9.2%) | 19 | 7.22 | 151.33 (±15) | 4.04 (±0.49) | 11.67 (±2.19) | Films are clear, transparent, uniform, and bendable |
| HA (65%): PVP (25%): PEG (10%) | 26.5 | 7.25 | 155 (±19.5) | 5.51 (±0.69) | 15.63 (±0.6) | Films are clear, transparent, uniform, and bendable |
| HA (85%): PVP (5%): PEG (10%) | 27.4 | 7.3 | 159 (±9.8) | 4.7 (±0.28) | 21.04 (±5.6) | Films are clear, transparent, uniform, and bendable |
| HA (90%): PVP (10%) | 30 | 7.2 | 190 (±2.6) | 6.4 (±0.39) | 13.5 (±4.9) | Films are clear, transparent, uniform, and bendable |

TABLE 3

HA/HP-GUAR/PVP/PEG COMBINATIONS

| Formulation | Dissolution time (min) | Surface pH | Modulus (MPa) | Tear strength (MPa) | % elongation | Description |
|---|---|---|---|---|---|---|
| HA (22.5%): HP-Guar (22.5%): PVP (45%): PEG (10%) | 14 | 7.32 | 110 ± 9.24 | 3.59 ± 0.42 | 33.85 ± 9.8 | Semi-transparent to opaque films |
| HA (30%): HP-Guar (30%): PVP (30%): PEG (10%) | 33 | 7.21 | 147 ± 3.61 | 5.33 ± 0.5 | 38.75 ± 9.0 | Semi-transparent to opaque films |
| HA (40%): HPguar (40%): PVP (10%): PEG (10%) | 37 | 7.2 | 174 ± 18 | 7.15 ± 0.45 | 19.38 ± 6.03 | Semi-transparent to opaque films |
| HA (42.5%): HP-Guar (42.5%): PVP (5%): PEG (10% | 53 | 7.23 | 160 ± 18 | 5.66 ± 0.75 | 18.33 ± 3.21 | Semi-transparent to opaque films |
| HA (45%): HP-Guar (45%): PVP (10%) | 52 | 7.2 | 258 ± 42 | 8.99 ± 1.25 | 20.42 ± 3.15 | Semi-transparent to opaque films |

TABLE 4

HA/HP-GUAR/PAA/PEG COMBINATION

| Formulation | Dissolution time (min) (not measured) | Surface pH (not measured) | Modulus (MPa) | Tear strength (MPa) | % elongation | Description |
|---|---|---|---|---|---|---|
| HA (22.5%): HP-Guar (22.5%): PAA (45%): PEG (10% | | | 229 ± 13.3 | 2.7 | 6.46 | Stiff films |

TABLE 4-continued

HA/HP-GUAR/PAA/PEG COMBINATION

| Formulation | Dissolution time (min) (not measured) | Surface pH (not measured) | Modulus (MPa) | Tear strength (MPa) | % elongation | Description |
|---|---|---|---|---|---|---|
| HA (30%): HP-Guar (30%): PAA (30%): PEG (10%) | | | 252 ± 13.89 | 4.41 | 7.29 | Stiff films |
| HA (40%): HP-Guar (40%): PAA (10%): PEG (10%) | | | 273 ± 9.71 | 6.82 | 6.5 | Stiff films |
| HA (42.5%): HP-Guar (42.5%): PAA (5%): PEG (10%) | | | 218 ± 10 | 7.2 | 10.00 | Stiff films |
| HA (45%): HP-Guar (45%): PAA (10%) | | | 190 ± 3.61 | 9.19 | 18.13 | Stiff Films |

TABLE 5

HA/HP GUAR/PEG COMBINATION WITH 200 PPM MENTHOL

| Formulation | Dissolution time (min) | Surface pH | Modulus (MPa) | Tear strength (MPa) | % elongation | Description |
|---|---|---|---|---|---|---|
| HA (45.4%): HP-Guar (45.4%): PEG (9.2%) | 66 | 7.15 | 189.35 | 10.56 | 16.67 | The films are transparent |
| HA (45.4%): HP-Guar (45.4%): PEG (9.2%): Menthol (200 ppm) | 20 | 7.19 | 248.32 | 7.63 | 11.46 | The films are opaque in the presence of menthol |
| HA (45.4%): HP-Guar (45.4%): PEG (9.2%): Menthol (100 ppm) | 47 | 7.15 | 187.67 | 7.99 | 18.13 | The films are opaque in the presence of menthol |

HA/HP Guar/PEG Film Characterization

Based on the data generated for the wide range of film compositions it was determined that a preferred polymer composition contained 45.4% hyaluronic acid (HA): 45.4% hydroxypropyl guar (HP guar): 9.2% polyethylene glycol (PEG 400) (referred to as Formulation 2 below). This film was prepared as follows:

TABLE 6

HA/HP GUAR/PEG COMBINATION

| Formulation 2 Film Composition | | Plasticizer | |
|---|---|---|---|
| Hyaluronic acid | Hydroxypropyl guar | Polyethylene glycol | Solvent Media Distilled water |
| 5.107 grams | 5.107 grams | 1.035 grams | 750 ml |

In a 1L Erlenmeyer flask, 750 ml of distilled water was poured into the flask followed by the addition of Hyaluronic Acid (5.107 grams). The flask was then placed into the sonicator and attached to an overhead mechanical stirrer. The mixture was allowed to stir and sonicate 30 minutes (±10 minutes) at a speed of 700 rpm at 25° C. to 35° C. until a homogeneous, clear solution was obtained. Hydroxypropyl guar (5.107 grams) was then added to the flask. The flask was placed back into the sonicator and attached to an overhead mechanical stirrer. The mixture was stirred and sonicated for 120 minutes (±10 minutes) at a speed of 700 rpm at 38° C. to 42° C. until a homogeneous, clear solution was obtained. The plasticizer, polyethylene glycol-400 (1.035 grams), was added into the flask. The mixture was allowed to stir and sonicate for 30 minutes (±10 minutes) at a speed of 700 rpm at 40° C. to 45° C. until a homogeneous, clear solution was obtained. The mixture was sonicated without stirring for an additional 30 minutes (±10 minutes) at 40° C. to 45° C. until a homogeneous, clear solution (no bubbles) was obtained. The flask was allowed to stand at room temperature for 30 minutes (±10 minutes). After proper mixing, the casting solution (150 g±2 g) was poured into a clean petri dish (150 mm×15 mm). The petri dish was dried at room temperature for 60 h (±5 h) in an evaporation chamber equipped with an exhaust fan. After drying, the disk was cut into 9 cm×9 cm pieces and kept in an airtight bag for 24 h (±3 h) under controlled humidity (<50%) and temperature (23° C. to 26° C.) levels for use in further characterization studies.

TABLE 7

FORMULATION 2 AVERAGE WEIGHT MEASUREMENTS

| Formulation-2 | Weight uniformity (mean ± SD) mg |
|---|---|
| F-2-50-2 | 4.425 ± 0.263 |
| F-2-50-3 | 4.258 ± 0.188 |
| F-2-50-4 | 4.492 ± 0.156 |
| F-2-50-5 | 4.575 ± 0.280 |

TABLE 8

FORMULATION 2 MOISTURE ABSORPTION MEASUREMENTS

| Formulation-2 | % Moisture Absorption (mean ± SD) |
|---|---|
| F-2-50-2 | 5.052 ± 0.211 |
| F-2-50-3 | 5.550 ± 0.289 |
| F-2-50-4 | 4.770 ± 0.327 |
| F-2-50-5 | 4.845 ± 0.606 |

TABLE 9

FORMULATION 2 MOISTURE LOSS MEASUREMENTS

| Formulation-2 | % Moisture loss (mean ± SD) |
|---|---|
| F-2-50-2 | 8.630 ± 0.433 |
| F-2-50-3 | 9.010 ± 0.608 |
| F-2-50-4 | 9.148 ± 0.515 |
| F-2-50-5 | 8.415 ± 0.323 |

TABLE 10

FORMULATION 2 FOLDING ENDURANCE MEASUREMENTS

| Formulation-2 | Folding endurance (mean ± SD) |
|---|---|
| F-2-50-2 | 38.50 ± 4.950 |
| F-2-50-3 | 42.50 ± 6.363 |
| F-2-50-4 | 37.50 ± 3.535 |
| F-2-50-5 | 36.50 ± 6.369 |

TABLE 11

FORMULATION 2 DISSOLUTION TIME AND PH MEASUREMENTS

| Formulation-2 | Dissolution time (min*) | | | pH | |
|---|---|---|---|---|---|
| | | Mean | SD | Mean | SD |
| F-2-50-2 | 17 | 16.25 | 0.957 | 7.19 | 7.023 0.210 |
| F-2-50-3 | 17 | | | 7.16 | |
| F-2-50-4 | 16 | | | 7.01 | |
| F-2-50-5 | 15 | | | 6.73 | |

TABLE 12

FORMULATION 2 TENSILE STRENGTH, MODULUS, AND PERCENT ELONGATION MEASUREMENTS

| | Tensile strength (N/cm2) | Modulus (N/cm2) | Displacement (from 3 cm) | % Elongation |
|---|---|---|---|---|
| Formulation-2 | 9.8 | 9.9 | 4.1 | 36.66 |
| | 10.10 | 9.9 | 3.9 | 30 |
| | 9.90 | 10.3 | 3.9 | 30 |
| | 10.10 | 10.2 | 4.2 | 40 |
| Mean | 9.975 | 10.075 | 4.025 | 34.17 |
| SD | 0.15 | 0.206 | 0.150 | 5.0 |

Example 3

Direct thickness measurement of the tear film is possible using HRA-OCT. HRA-OCT imaging was used to provide a measurement of the tear film thickness following insertion of the insert and this indirectly indicates the effect resulting from the delivery of lubricant (i.e., enhancement of the tear film thickness indicates delivery of lubricant and/or drug). Following insertion the insert is expected to slowly dissolve and release lubricant and/or drug. The general method used is described below using New Zealand rabbits. In this procedure, an insert using 45.4% Hydroxypropyl guar (HP guar) and 9.2% Polyethylene glycol (PEG 400) was evaluated in rabbits using HRA-OCT. On Day 1, a single insert was placed into the central, lower cul-de-sac of the right eye with forceps or another appropriate device. Treatment was repeated on Day 3 with inserts applied to the left eye. The study treatment design is summarized in TABLE 13.

TABLE 13

EXAMPLE STUDY DESIGN

| Group No. | Animal No. | Treatment* | Dosing Regimen | Observation Period |
|---|---|---|---|---|
| 1 | 3 | TA1 | One (1) insert on Day 1 in the right eye. One (1) insert on Day 3 in the left eye | Day 3 after the last ophthalmic evaluation |
| 2 | 3 | TA2 | | |
| 3 | 3 | TA3 | | |

Animals undergo optical coherence tomography (OCT) scans at various time points up to 3 hours if needed. The method for OCT imaging and image analysis in the rabbit is as follows:

1. Lighting was dimmed in the imaging room to facilitate imaging.
2. Lightly brush below the eye to be imaged with a cotton-tipped applicator to induce a natural blink response.
3. Capture one horizontal image centered at the apex of the cornea.
4. Lightly brush below the eye again with a cotton-tipped applicator to induce a natural blink response.
5. Capture one vertical image centered at the apex of the cornea.
6. Document dose information and image numbers.
7. Determine 3 points on each image for analysis (horizontal: nasal, apex, temporal region of the eye; vertical: top, apex, bottom of the eye).
8. Use the measurement tool on the Bioptogen to determine tear film thickness at each analysis point and document measurements.

Treatment groups and imaging schedules for the test animals are presented below in TABLES 14 and 15.

TABLE 14

TREATMENT GROUPS

| Group No. | Treatment | Hydration Drop (BSS) | No. of Animals |
|---|---|---|---|
| 1 | BSS | 30 uL dose every 15 minutes | 4 |
| 2 | 45.42% Sodium-HA/45.42% HP-Guar/9.16% PEG400 Insert | 30 uL dose every 15 minutes | 4 |
| 3 | 45.42% Sodium-HA/45.42% HP-Guar/9.16% PEG400 Insert | 30 uL dose at insertion | 4 |
| 4 | Lacrisert | N/A | 4 |

TABLE 15

GROUP IMAGING SCHEDULE

| Group | Imaging Schedule |
|---|---|
| 1 | Pre-dose<br>Immediately Post-Dose<br>15 and 30 Min Post 1$^{st}$ Dose |
| 2 | Pre-dose<br>Immediately Post-Dose<br>15, 30, 45, 60, 75 & 90 Min Post-Dose |
| 3 | Pre-dose<br>Immediately Post-Dose<br>15, 30, 45, 60, 75, 90, 105, 120, 135 & 150 Min Post-Dose |
| 4 | Pre-dose<br>Immediately Post-Dose<br>15, 30, 45, 60, 75, 90, 105, 180 & 360 Min Post-Dose |

Figure 9:
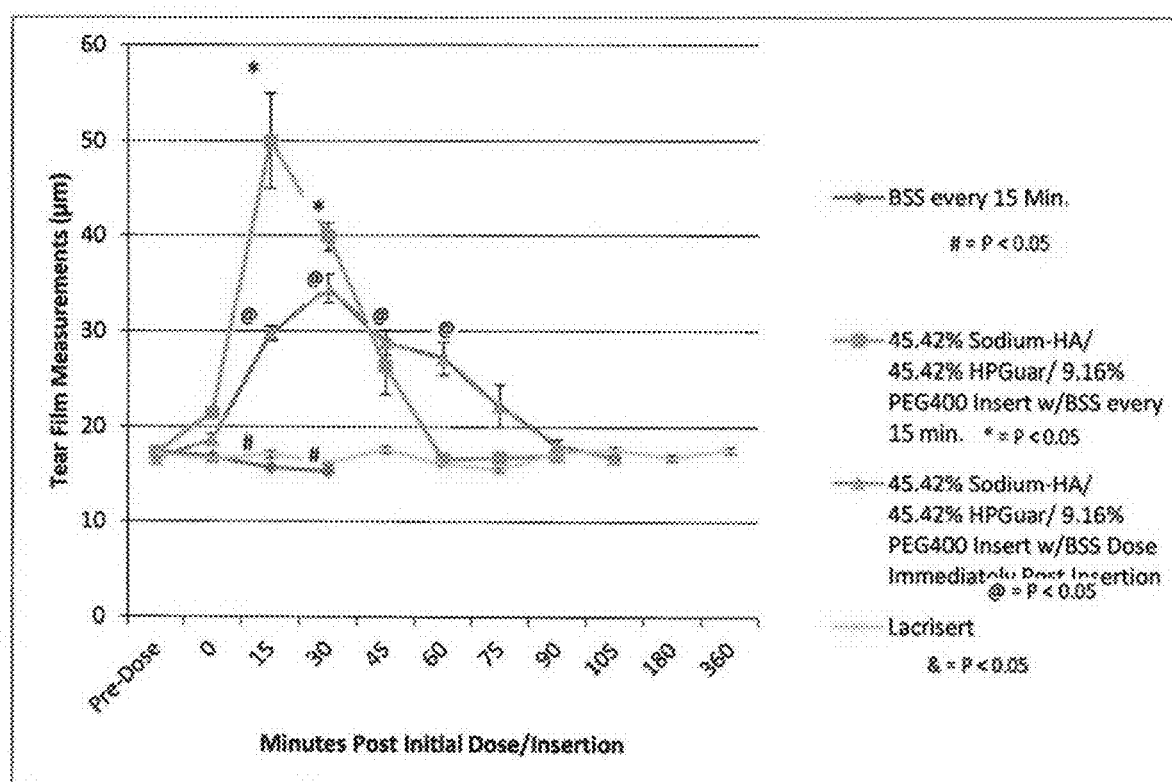
FIG. 9 reflects tear film thickness data as a function of elapsed time post-dose.

FIG. 9 presents the tear film thickness data from the testing. In this test LACRISERT® was used as a control. In this in vivo experiment there were no significant issues associated with safety or tolerability with LACRISERT® and the test articles containing HPGuar/HA/PEG. In this in vivo test the test articles were exposed to two different post-dosing regimens. In one case following insertion the BSS was added every 15 min to try and accelerate the dissolving insert. In the second case BSS was dosed once following the insert insertion. The LACRISERT® was simply inserted as per instructions for the human eye. The OCT measurements showed an increase in tear film thickness for the test articles for both scenarios. The BSS addition accelerated the dissolving insert as showed by the rapid increase in tear film thickness around 5 min to a max tear film thickness of 50 microns after 15 min. Comparatively, the scenario with a single post insertion drop showed the tear film thickness to extend across 90 min followed by decrease to baseline within 2 hours. The LACRISERT® during this time frame showed no noticeable effects on the tear film thickness and following 3 hours it remained in a solid-like state. The HA/HPG/PEG insert test articles were completely dissolved after 2 hours in this experiment.

Example 4

Inserts With Pharmaceutically Active Agents

The inserts of the present invention may include one or more pharmaceutically active agents, as detailed supra. An insert film prepared with an anti-muscarinic, atropine, is provided below.

Eye Insert Preparation With Atropine

40% Hyaluronic acid (HA): 40% hydroxypropyl guar (HP): 10% Polyethylene glycol (PEG 400): 10% Polyvinyl pyrrolidone: 500 ppm Atropine

TABLE 17

ATROPINE INSERT FORMULATION

| Film formulation | | Plasticizer | | | Solvent |
|---|---|---|---|---|---|
| Hyaluronic acid | Hydroxy-propyl guar | Polyvinyl pyrrolidone (Aldrich) | Polyethylene glycol (Aldrich) | Drug Atropine (Aldrich) | Media Distilled water |
| 2.1 g | 2.1 g | 0.525 g | 0.525 gm | 0.175 g | 350 ml |

Procedure:

To prepare 350 g of the insert formulation the following quantities are needed: HA (2.1 g): HP-guar (2.1 g): PEG-400 (0.525 g): PVP (0.525 g): Atropine (0.175 g) in 350 ml distilled water. In 1L Erlenmeyer flask, 350 ml distilled water was mixed with 2.1 g Hyaluronic acid and 0.525 g polyvinyl pyrrolidone. The flask was attached to an overhead mechanical stirrer and the mixture was stirred at 600 RPM for 30 minutes at 35° C. Then 2.1 g Hydroxypropyl guar was added. The mixture was then stirred for 120 minutes at 38° C. until a homogeneous clear solution is obtained. The plasticizer polyethylene glycol-400 (0.525 g) and Atropine (0.175 g) were then added into the flask and the mixture was stirred for another 30 minutes at 700 RPM. The mixture was left to cool down for 30 minutes. At this stage the solution was ready for film casting.

Film Casting:

150 g±2 g of the solution was poured into clean petri dish (150 mm×15 mm). The petri dish was dried for 30 h at room temperature for 30 h using a drying chamber. The obtained film was clear and did not show any crystallization or unusual visual appearance.

Eye Insert Preparation With Povidone Iodine

In another example, a broad spectrum biocide povidone iodine was utilized with the insert. This insert had the following formulation: 40% Hyaluronic acid (HA): 40% hydroxypropyl guar (HP): 10% Polyethylene glycol (PEG 400): 10% Polyvinyl pyrrolidone and 500 ppm PVP-I in the total mass.

Procedure:

Procedure for preparing 350 g batch of the formulation in 1L Erlenmeyer flask with concentration 0.015 g/mL. HA (2.1 g): HP-guar (2.1 g): PEG-400 (0.525 g): PVP (0.525 g): PVP-I (0.175 g) in 350 ml distilled water. In 1L Erlenmeyer flask, 350 mL distilled water, Hyaluronic acid (2.1 g) and polyvinyl pyrrolidone (0.525 g) was added. The flask was placed into the sonication bath and attached to overhead mechanical stirrer. The mixture was stirred and sonicated at the same time for 30 minutes (±10 minute) at a speed of 600 RPM and at a temperature between 25° C. to 35° C. until a homogeneous clear solution was obtained. The Hydroxypropyl guar (2.1 g) was then added. The flask content was stirred for 120 minutes (±10 minute) at a speed of 600 RPM and at a temperature between 38° C. to 41° C. until a homogeneous clear solution was obtained. The polyethylene glycol-400 (0.525 g) and PVP-I (0.175 g) were then added into the flask. The mixture was stirred for extra 45 minutes. 150 gm±2 g of the solution was poured in a clean petri dish (150 mm×15 mm). The petri dish was dried at room temperature for 30 h (±1 h) in a ventilated chamber. 500 ppm of PVP-I was calculated based on the total mass including water.

Example 5

Tear film measurements for polymeric eye inserts according to embodiments of the present disclosure were also compared to tear film measurements of SYSTANE® ULTRA eye drops as well as GENTEAL® gel eye drops and PROVISC® injectable.

FIGS. 2A-2C depict tear film measurements for the SYSTANE® ULTRA eye drops pre-dose (FIG. 2A), immediately post-dose (FIG. 2B) and 5 minutes post-dose (FIG. 2C). FIGS. 2A-2C reflect that the tear film measures 22 μm pre-dose, 60 μm immediately post-dose, and 19 μm 5 minutes post-dose.

FIGS. 3A-3C depict tear film measurements for the GENTEAL® gel eye drops pre-dose (FIG. 3A), immediately post-dose (FIG. 3B) and 5 minutes post-dose (FIG. 3C). FIGS. 3A-3C reflect that the tear film measures 20 μm pre-dose, 31 μm immediately post-dose, and 19 μm 5 minutes post-dose.

Figure 4E:
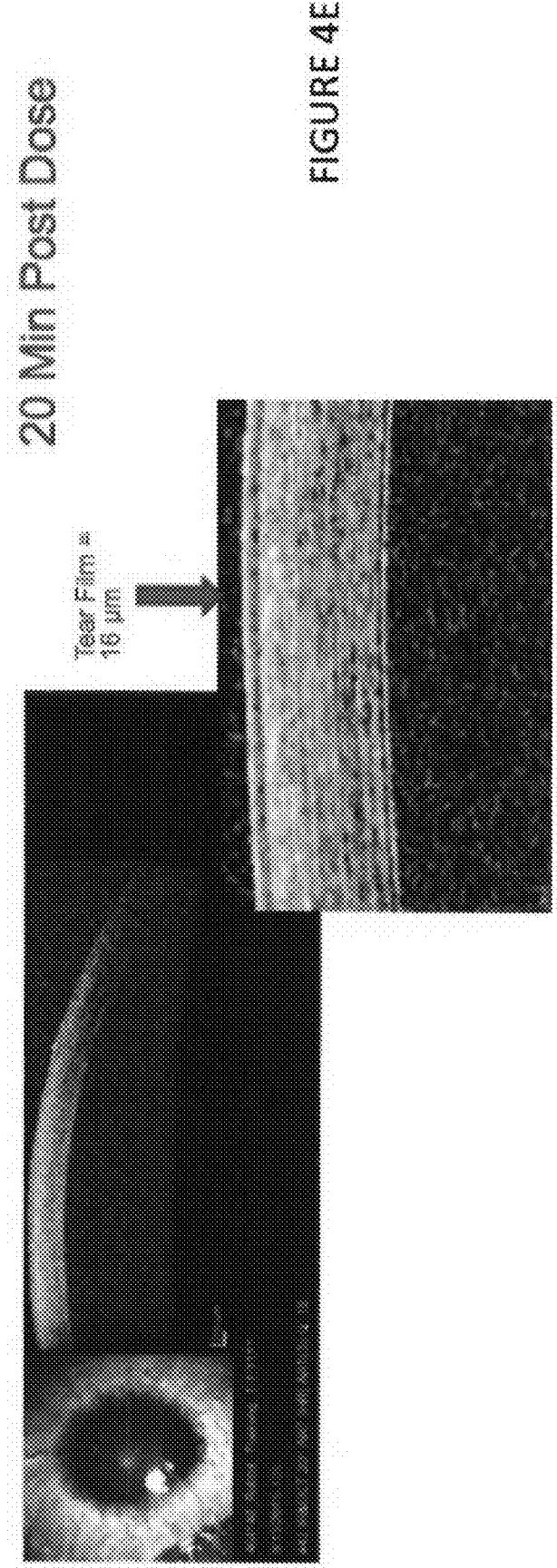

FIGS. 4A-4E depict tear film measurements for the PROVISC® injectable pre-dose (FIG. 4A), immediately post-dose (FIG. 4B), 5 minutes post-dose (FIG. 4C), 10 minutes post-dose (FIG. 4D) and 20 minutes post-dose (FIG. 4E). FIGS. 4A-4E reflect that the tear film measures 19 μm at pre-dose, 194 μm immediately post-dose, 114 μm at 5 minutes post-dose, 61 μm at 10 minutes post-dose, and 16 μm at 20 minutes post-dose.

Each of the tear film measurements set forth in FIGS. 2A-2C, 3A-3C, and 4A-4E reflect the tear film increases in thickness immediately post-dose but returns to a thickness similar to that measured pre-dose within anywhere from 5 to 20 minutes post-dose.

In contrast, FIGS. 5A-5I reflect tear film measurements associated with insertion of a polymeric eye insert according to embodiments of the present disclosure. These measurements reflect that the tear film measures 14 μm pre-dose (FIG. 5A), 20 μm 15 minutes post-dose (FIG. 5B), 81 μm 30 minutes post-dose (FIG. 5C), 45 μm 45 minutes post-dose (FIG. 5D), 43 μm 1 hour post-dose (FIG. 5E), 37 μm 1 hour and 15 minutes post-dose (FIG. 5F), 33 μm 1 hour and 30 minutes post-dose (FIG. 5G), 22 μm 1 hour and 45 minutes post-dose (FIG. 5H), and 18 μm 2 hours post-dose (FIG. 5I). Accordingly, in this embodiment of the present disclosure, the tear film thickness does not return to its pre-dose thickness until approximately 2 hours post-dose.

Additional tear film measurements were performed on New Zealand white rabbits. Each rabbit received a single polymeric eye insert. 3 horizontal and 3 vertical images were obtained per time point. Three points on each line were measured and zoomed in to 800% to determine the depth of the tear film/test article.

Figure 6A:
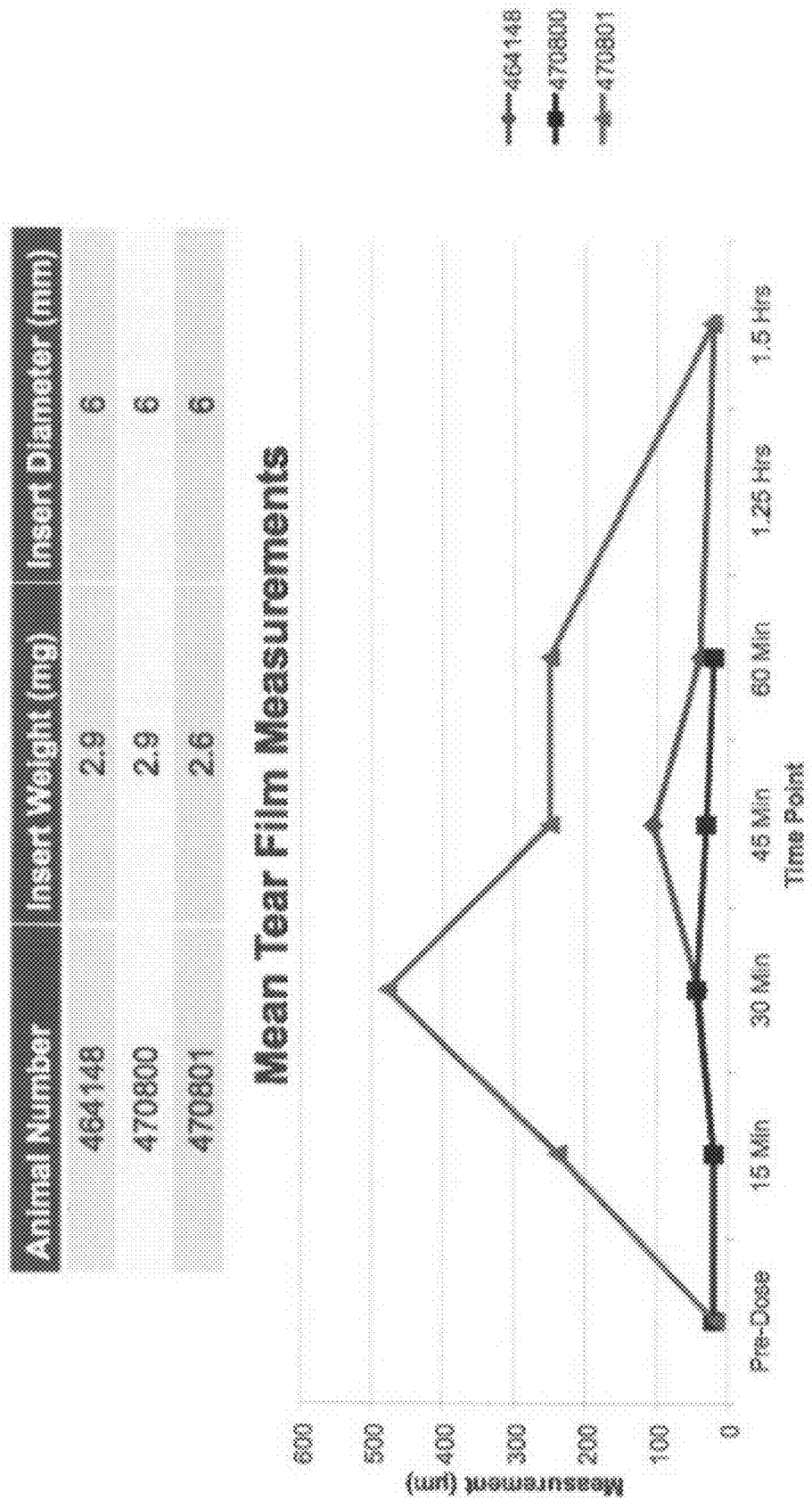
FIG. 6A reflects mean tear film measurements using polymeric eye inserts according to an embodiment of the present disclosure.
Figure 6B:
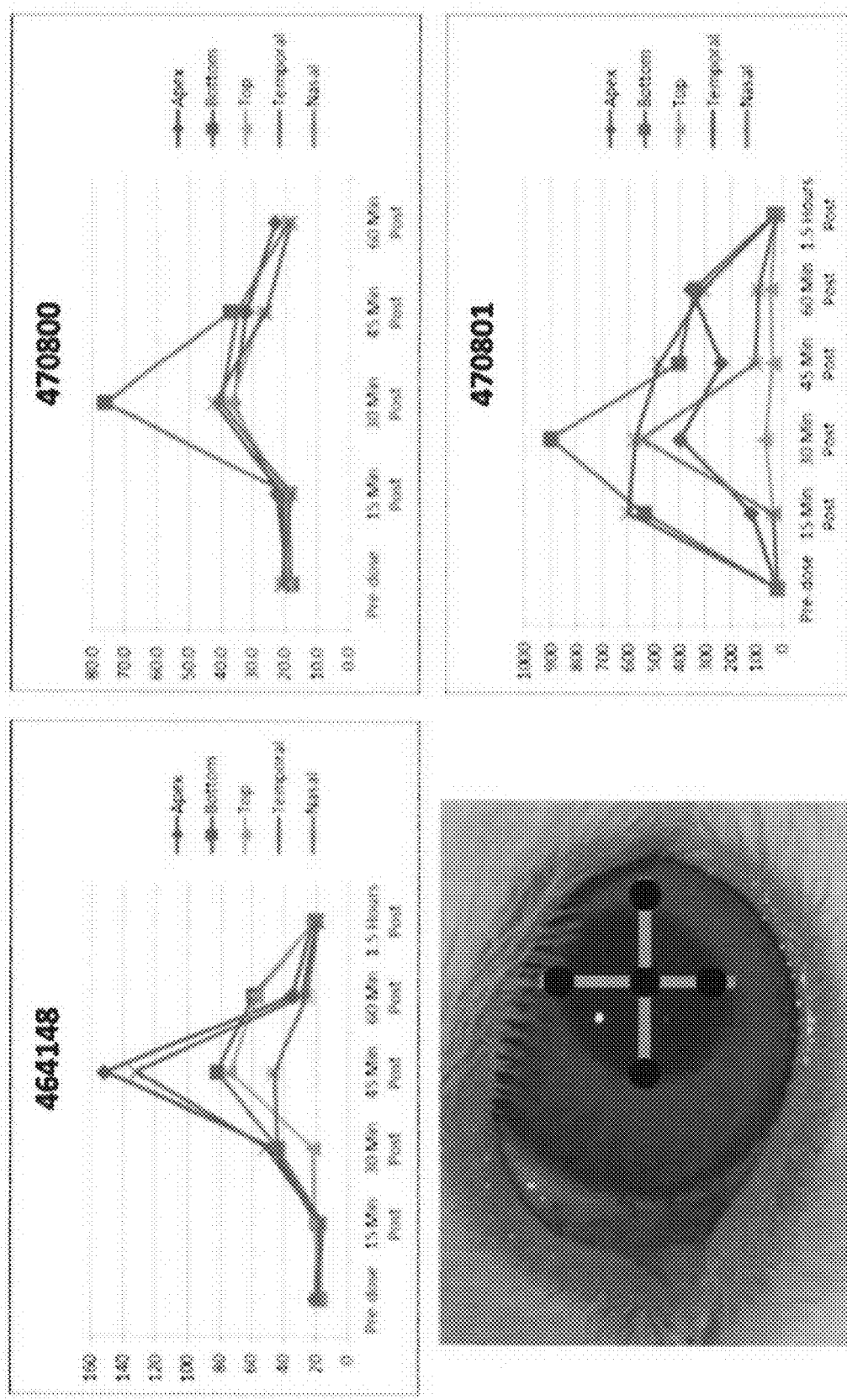
FIG. 6B reflects tear film measurements by individual animal according to an embodiment of the present disclosure.
Figure 6C:
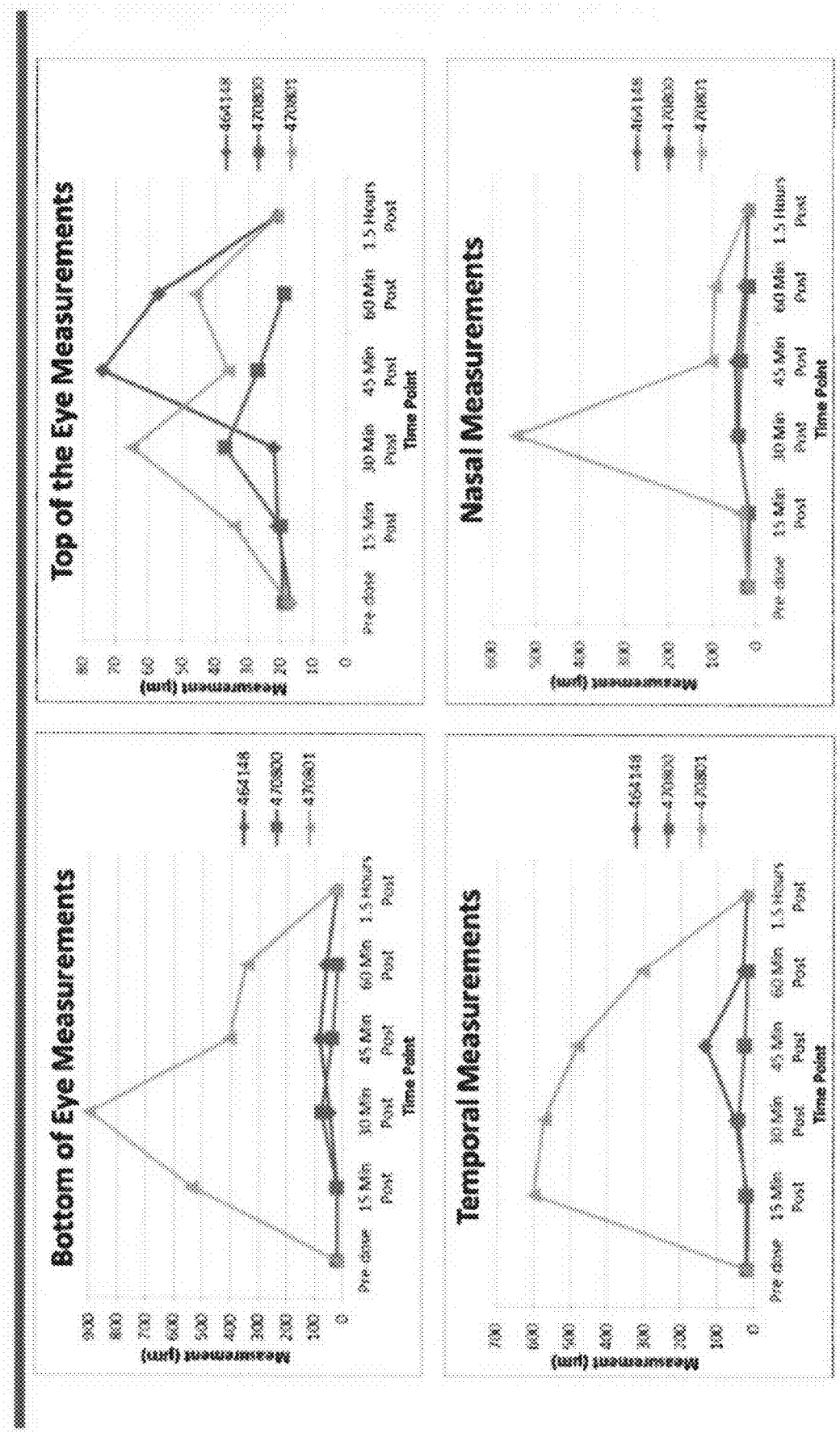
FIG. 6C reflects tear film measurements based on location in the eye including the bottom of the eye, top of the eye, temporal and nasal measurements according to an embodiment of the present disclosure.

FIG. 6A reflects mean tear film measurements using polymeric eye inserts according to embodiments of the present disclosure. Three rabbits were tested, and each rabbit blinked three times prior to image capture. The insert diameter (6 mm) remained the same across testing of each rabbit, and the insert weight ranged from 2.6 mg to 2.9 mg. FIG. 6B reflects tear film measurements by individual animal. FIG. 6C reflects tear film measurements based on location in the eye including bottom of the eye, top of the eye, temporal and nasal measurements.

Figure 7A:
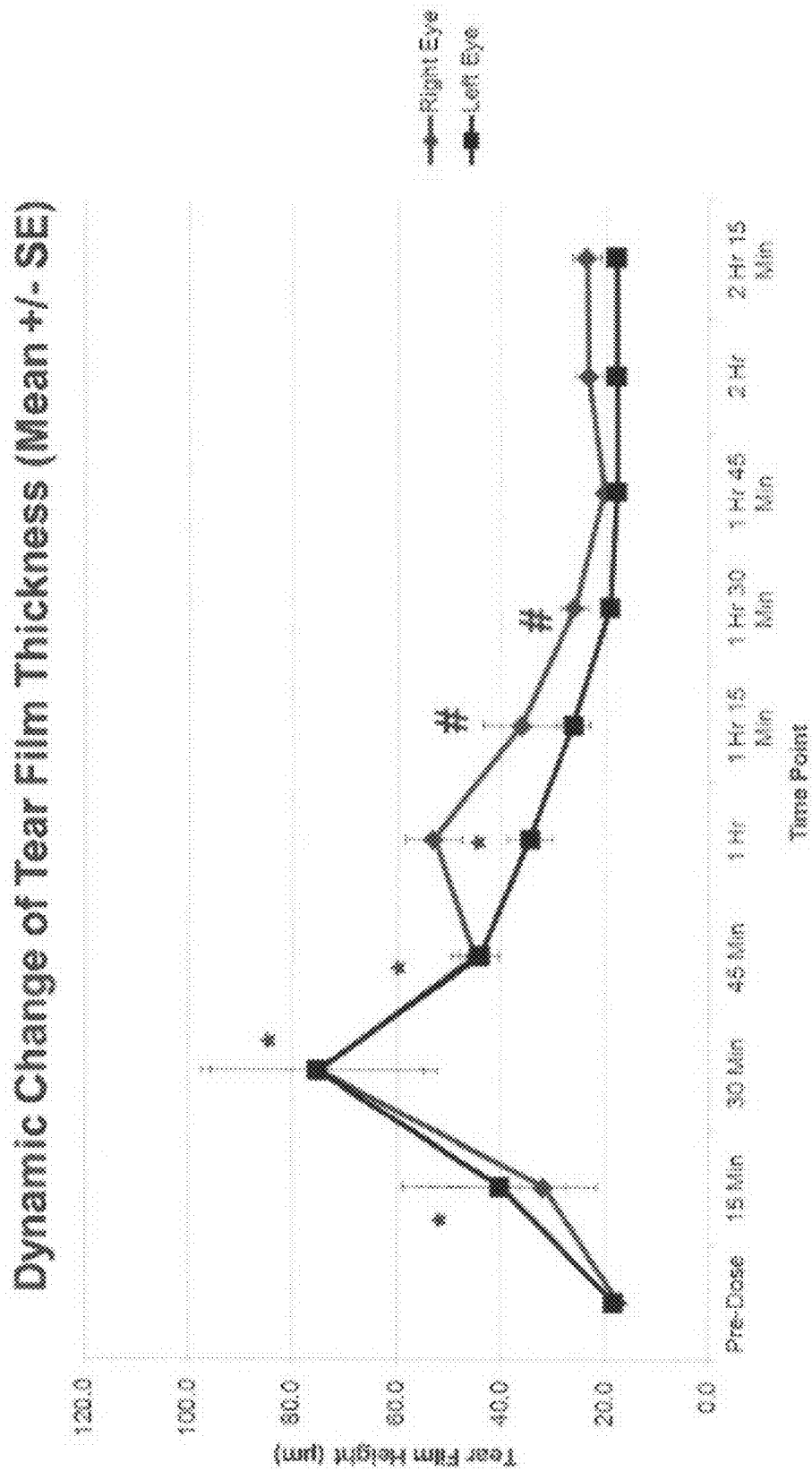
FIG. 7A reflects the dynamic change of tear film thickness with respect to polymeric eye inserts according to embodiments of the present disclosure.
Figure 7B:
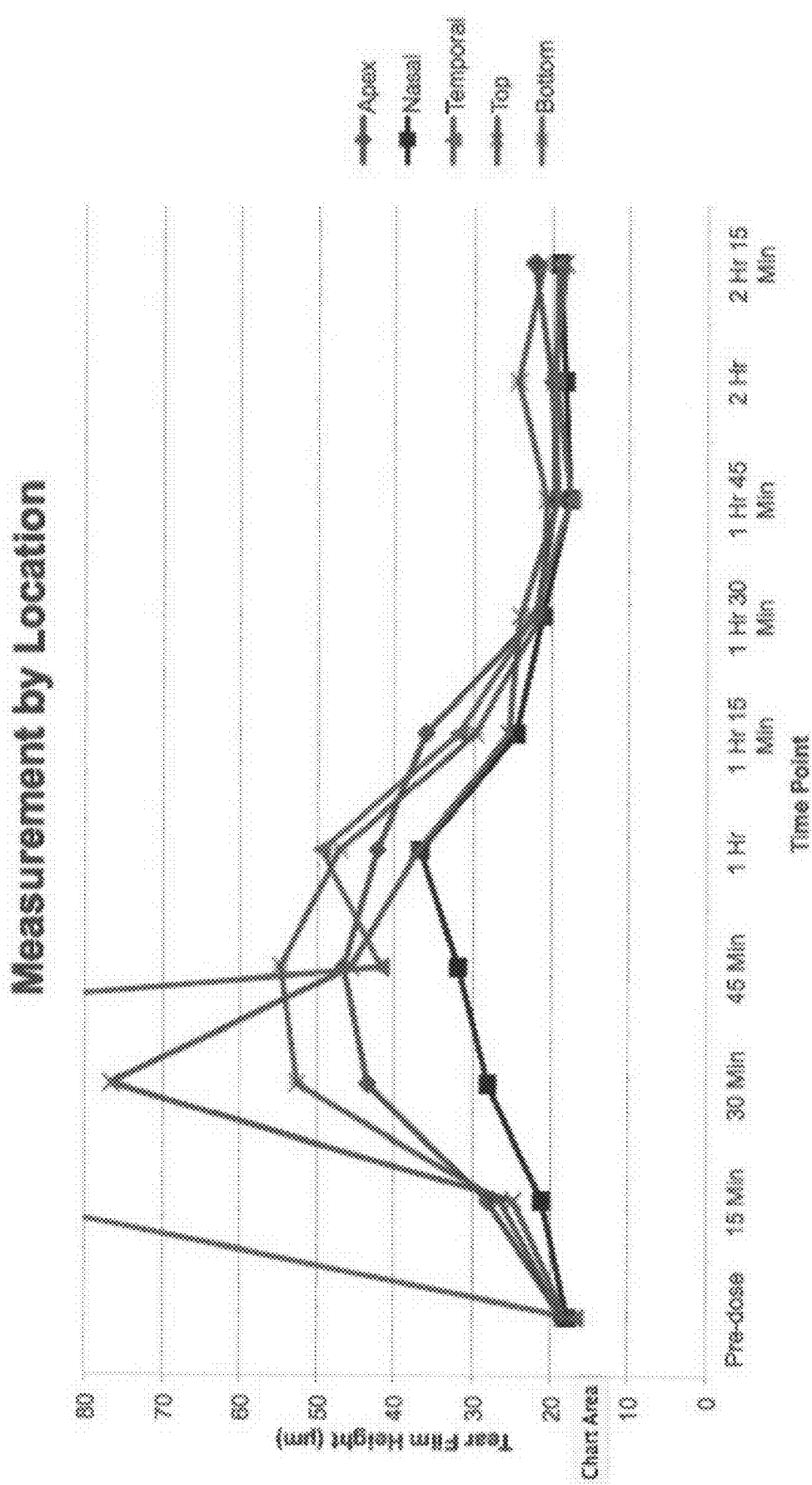
FIG. 7B reflects tear film measurements by location (apex, nasal, temporal, top, and bottom) for polymeric eye inserts according to embodiments of the present disclosure.

Further testing on New Zealand white rabbits measured the dynamic change of tear film thickness associated with polymeric eye inserts according to embodiments of the present disclosure (FIG. 7A). The insert diameter remained at 6 mm. The insert weight for oculus sinister (OS) ranged from 3.2 to 3.8 mg, and the insert weight for oculus dextrus ranged from 2.2 to 2.6 mm. FIG. 7B reflects tear film measurements by location (apex, nasal, temporal, top, and bottom).

Figure 8:
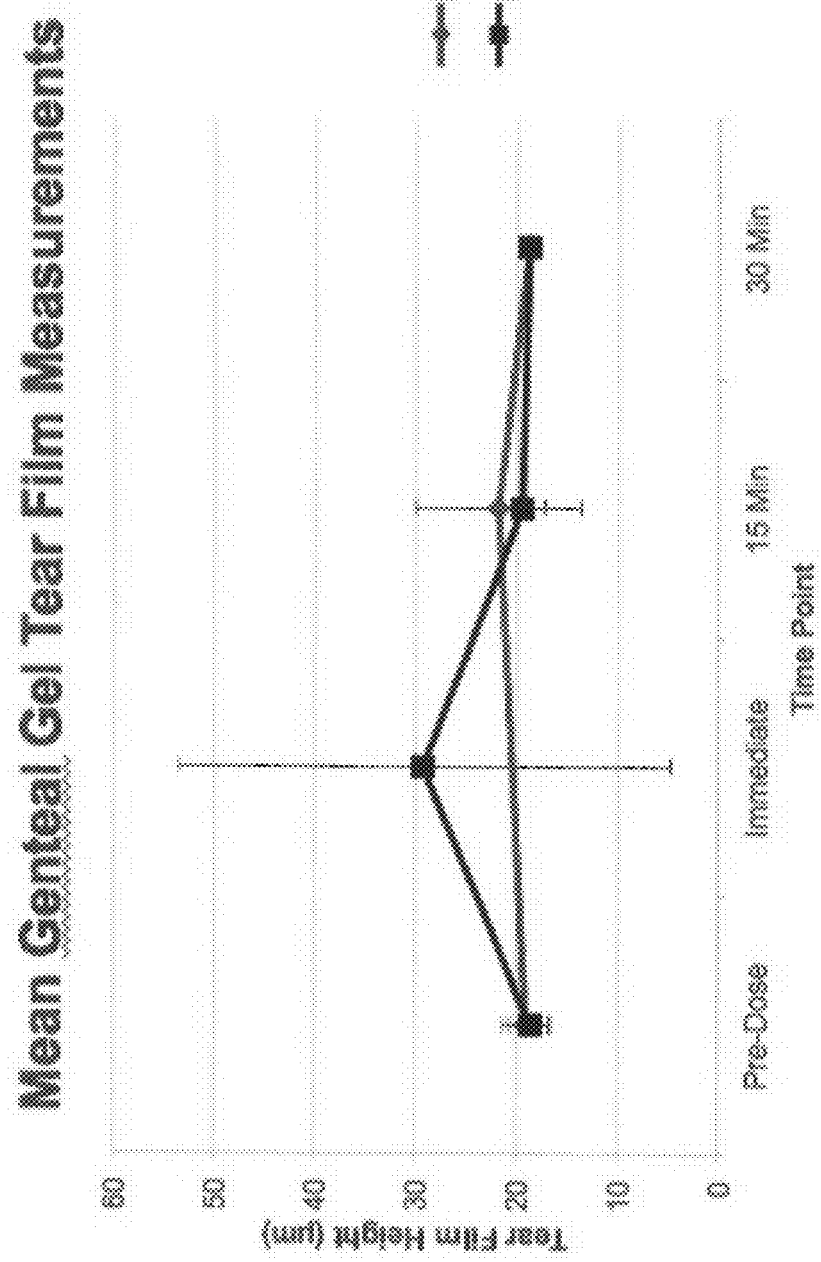
FIG. 8 reflects mean GENTEAL® gel tear film measurements for the right and left eye.

This testing also made similar measurements with respect to GENTEAL® gel at a dosage of 80 μL or approximately 76.3 mg into the central lower cul-de-sac of the eye. FIG. 8 reflects mean GENTEAL® gel tear film measurements for the right and left eye.

After taking measurements for both the polymeric eye insert according to embodiments of the present disclosure and GENTEAL® gel, the results were analyzed. TABLE 18 below reflects the number of animals with a mean of 6 readings greater than or equal to 30 μm.

TABLE 18

| Test Article | Minutes Post Dose | | | | | | | | |
|---|---|---|---|---|---|---|---|---|---|
| | 15 | 30 | 45 | 60 | 75 | 90 | 105 | 120 | 135 |
| Genteal Gel (microns) | 1 | 0 | 0 | 0 | 0 | 0 | 0 | 0 | 0 |
| Eye Insert (microns) | 3 | 6 | 7 | 5 | 2 | 1 | 0 | 1 | 1 |

This testing confirmed that tear film thickness change can be effectively monitored through Spectralis HRA+OCT. Inserts begin to dissolve by 15 minutes post-dose in most animals. Most animals dosed with a polymeric eye insert according to embodiments of the present disclosure had a significant increase of tear film thickness for at least 30 minutes post-dose. It should be appreciated that the location of the polymeric eye insert, both initial placement and movement after blinking, may create variations in data, particularly in early time points; however, IR image and OCT can help to differentiate the influence of insert location. It also should be appreciated that the weight of the insert may have an impact on length of retention. Further, it should be appreciated that intrinsic differences among animals may impact the results. For example, one animal had the longest duration of increased tear film thickness regardless of insert size; however, the larger insert retained approximately 45 minutes longer. It also was noted that aqueous solutions caused little tear film thickness changes.

As reflected through the studies described above, a polymeric eye insert according to an embodiment of the present disclosure may assume the form of a dissolvable film comprised of hydrophilic polymers with high mucoadhesive and H-bonding properties. The film may contain one or more naturally derived polysaccharides or synthetic polymers that are biocompatible and well-tolerated by the eye. The dissolvable film may have a thin film design that may allow for easy, comfortable insertion into the cul-de-sac of the eye, as the film should be small enough to fit into the cul-de-sac with little-to-no irritation upon insertion but large enough so that dissolution occurs over a longer period of time. Such a dissolvable film may hydrate quickly to form a soluble gel and release lubricant and/or a pharmaceutically active agent within a short time frame (e.g., the first 5-10 minutes following insertion). This slow pulsed flow of lubricant may maximize the adhesion and residence time of the lubricant on the ocular surface as compared to topical drop usage. The retention time of the lubricant on the eye may be increased by slow delivery in the tear film and ocular surface.

Insertion of a dissolvable film according to embodiments of the present disclosure does not lead to visual disturbances after several minutes. It should be appreciated that the dissolvable film may retain a lubricant for approximately two hours or more; however, there may be embodiments of the present disclosure where retention may occur over approximately 30-60 minutes. Accordingly, a dissolvable film or polymeric eye insert according to embodiments of the present disclosure may provide advantages, including but not limited to, quick dissolution for reduced blurring, a thin film design for enhanced wetting kinetics and ocular tolerability, improved comfort on insertion, and reduced foreign sensation. Further, tolerability and delivery of lubricant may be improved as compared to other topical delivery systems or inserts.

While embodiments of the present disclosure have been described for use as lubricants and/or pharmaceutically active agents to treat dry eye, it should be appreciated that polymeric eye inserts according to embodiments of the present disclosure also may have advantages for ophthalmic delivery of pharmaceutically active agents to treat other ocular disorders. A non-exhaustive list of such disorders includes ocular hypertension, glaucoma, glaucomatous retinopathy, optic neuropathy, macular degeneration, diabetic retinopathy, choroidal neovascularization, proliferative vitreoretinopathy, ocular wounds and infections, and myopia.

While some embodiments have been described as films, it should be appreciated that a polymeric eye insert according to embodiments of the present disclosure can assume a variety of shapes including, but not limited to, films, rods and spheres. In an embodiment of the present disclosure, a circular film of approximately 0.5 to 10 mm diameter may be employed. In other embodiments, circular films of 4-7 mm diameter are particularly preferred. Various other film shapes may be used in certain embodiments, such as those presented in FIGS. 10A-10C.

Regardless which shape the insert assumes, a polymeric eye insert according to embodiments of the present disclosure should be small enough to fit into the cul-de-sac of the eye and be rapidly wetted so that there is little or no irritation upon insertion. The insert also should be large enough to allow for dissolution over anywhere from approximately 30-120 minutes to allow for release of the lubricant(s) and/or pharmaceutically active agents to occur. The insert should also have a thickness that is relatively comfortable for the user. A preferred thickness is between 50-250 microns, and a most preferred thickness is between 70-150 microns. The target thickness is 90 microns for films dissolving in less than 2 hours.

Example 6

Monkey Tolerability Study

The cynomolgus male monkey of Chinese origin (protein-naïve) was selected for this study based on the pharmacological and anatomical relevance of the monkey eye and following tolerance assessment in rabbit. The monkey eye blinks with similar frequency to the human. Clinical observations were performed for tolerability of the ocular test article at 15, 30, 45, 60, 120, 180, and 240 minutes post-dose. Special attention was afforded to tear film retention and tolerability. Gross examinations include tearing, redness, swelling, and blinking. At 24 hours post dose, animals in Groups 1 and 2 are lightly sedated and the treated eye is thoroughly examined for any presence of the tear film. If any tear film is detected, it is noted in the clinical observations and the remaining film removed. Additional clinical observations are noted as necessary if abnormalities continue past the final observation time point. If any unexpected clinical signs are present, the veterinarian is notified immediately. Animals are restrained manually, chemically (Ketamine or alternative e.g., Telazol, if needed, per Veterinary Guidelines), or mechanically (chair). Dosing is with light sedation. Observations are performed on lightly sedated or awake animals. The test articles are administered to lightly sedated animals (Ketamine 5-15 mg/kg, IM or alternative [e.g., Telazol 5-10 mg/kg, IM]). The time of dose administration is considered as the completion of dosing to the one eye. Once lightly sedated, a single insert test article is placed into the central, lower cul-de-sac of the left eye of all animals with forceps or another appropriate device.

Eye insert disks are composed of 40% HPGuar/40% HA/10% PVP/10% PEG and are labelled as TA1 and TA2. TA1 has a diameter of 6 mm and a thickness of 86 microns (std. deviation is 8.4 microns). TA2 has a diameter of 6 mm and a thickness of 108 microns (std. deviation is 8.3 microns). SYSTANE ULTRA® is used as the control.

OBSERVATIONS AND CONCLUSIONS

Following T=0 dosing, the thinner TA1 inserts were harder to place and they tended to fold once they touched the moisture on the tissue but once situated they lay flat without much trouble. The thicker films, TA2, did not fold and were easy to insert and lay flat immediately on the tissue. Both Groups TA1 and TA2 had mild to moderate tearing after insertion (the animals that received the drops had no tearing). There have been no signs of irritation, no redness, no eye rubbing and no other squinting observed over three hours. After 24 hours, no residual insert material was present in any animal and all of the treated eyes looked acceptable compared to the SYSTANE ULTRA® topical drop, with no redness, swelling or any other signs of irritation.

Example 7

Human Study of a Lubricant Polymeric Eye Insert

In order to assess the biocompatibility, safety, and tolerability of an polymeric eye insert, a study of an embodiment of the present disclosure was tested in a randomized, crossover design in human participants. Over the course of one study day, a total of three treatments were applied to each participant: 2 polymeric eye inserts and one ocular lubricant drop. Treatments were applied to one eye only, with the fellow untreated eye acting as the control eye.
Study Design:

Ten participants enrolled in the study (5 female, 5 male). The mean age of the participants was 35.5 years (median 33 years, ranging from 23 to 61 years).

The outcome measures for the study were as follows:
Primary outcome variable: Subjective rating of ocular comfort.

Secondary outcome variable: Subjective rating of visual blur, polymeric eye insert dissolution rate, Investigator rating of handling and non-invasive tear break-up time (NIT-BUT).

The study was conducted as follows: The study day lasted approximately 9 hours and included a screening and eligibility check, insertion of the first treatment (polymeric eye insert or ocular lubricant drop) into 1 eye, assessments, and eye rinse approximately 2 hours after insertion. After waiting for a minimum of 1 hour, the second treatment was applied to the other eye (eye not previously used) and procedures repeated. There was a wait of a minimum of 1 hour before the final treatment was applied and procedures repeated. For each treatment, ocular comfort and vision ratings were completed: prior to insertion, 5, 15, 30, 60, 90, and 105 minutes after insertion to assess tolerability of the treatment. Tear film assessments were carried out 5, 60, 90 and 105 minutes after insertion. Ocular safety measurements were carried out at screening and after each treatment. At the end of the study day, participants were asked to indicate their treatment preference.

Study Materials:

The two different polymeric eye inserts are as follows:

TABLE 19

|  | polymeric eye insert 1 (Thick insert) | polymeric eye insert 2 (Thin insert) |
|---|---|---|
| Ingredients | Hydroxypropyl Guar (HPGuar) 40% | Hydroxypropyl Guar (HPGuar) 40% |
|  | Hyaluronic Acid (HA) 40% | Hyaluronic Acid (HA) 40% |
|  | Polyvinylpyrrolidone/ Polyethylene Glycol (PVP/PEG) 10% | Polyvinylpyrrolidone/ Polyethylene Glycol (PVP/PEG) 10% |
| Other information | UV sterilised | UV sterilised |
| Diameter | 6 mm circular shape | 6 mm circular shape |
| Thickness | 135-145 μm | 105-115 μm |

Ocular lubricating drops (Systane) were used as a control treatment. The components of the ocular lubricating drops are as follows:

| Ingredients | Hydroxypropy Guar (HPGuar), Polyethylene Glycol (PEG) 400 0.4%, Propylene Glycol 0.3% |
|---|---|
| Preservative and disinfectant/ cleaning agent | POLYQUAD (polyquaternium-1) 0.001% w/v |

This study took place over one study day. During the study day, participants were asked to attend five scheduled visits.

Visit 1: Screening and eligibility (0.75 hrs)
Visit 2: Treatment 1 insertion, assessments and removal (2.0 hrs)
Visit 3: Treatment 2 insertion, assessments and removal (2.0 hrs)
Visit 4: Treatment 3 insertion, assessments and removal (2.0 hrs)
Visit 5: Study Exit (0.25 hrs).

A one-hour washout period was applied between visits 2 and 3, and between 3 and 4.

The procedures at each visit are summarized in Table 20

TABLE 20

Study visits and Procedures

| Measurement & processes | Screening & Eligibility (0.75 hrs) | Treatment insertion & assessment (2 hrs/treatment) | Study Exit (0.25 hrs) |
|---|---|---|---|
| Informed Consent | ✓ |  |  |
| Demographics | ✓ |  |  |
| Medical history | ✓ | ✓ |  |
| VA (logMAR) with spectacles | ✓ | ✓ | ✓ |
| Full slit lamp biomicroscopy | ✓ |  | ✓ |

TABLE 20-continued

Study visits and Procedures

| Measurement & processes | Screening & Eligibility (0.75 hrs) | Treatment insertion & assessment (2 hrs/treatment) | Study Exit (0.25 hrs) |
|---|---|---|---|
| Partial slit lamp biomicroscopy |  | ✓ |  |
| Confirm eligibility | ✓ |  |  |
| Treatment insertion |  | ✓ |  |
| Treatment removal |  | ✓ |  |
| Subjective ratings (questionnaires) | ✓ | ✓ |  |
| Investigator ratings (ease of insertion) |  | ✓ |  |
| Tear film meniscus height |  | ✓ |  |
| Non-invasive tear film break-up time with a placido disk device |  | ✓ |  |
| Assessment of polymeric eye insert |  | ✓ |  |

Study Results:

Primary outcome variable—comfort rating

At each of the time points (prior to insertion, 5, 15, 30, 60, 90, and 105 minutes after insertion), participants were asked the following question, "How would you rate the comfort of your eyes?".

Participants responded using a 0 to 100 scale where 0 indicates "Very poor comfort" and 100 indicates "Excellent comfort". The results are provided in FIG. 11.

Figure 11:
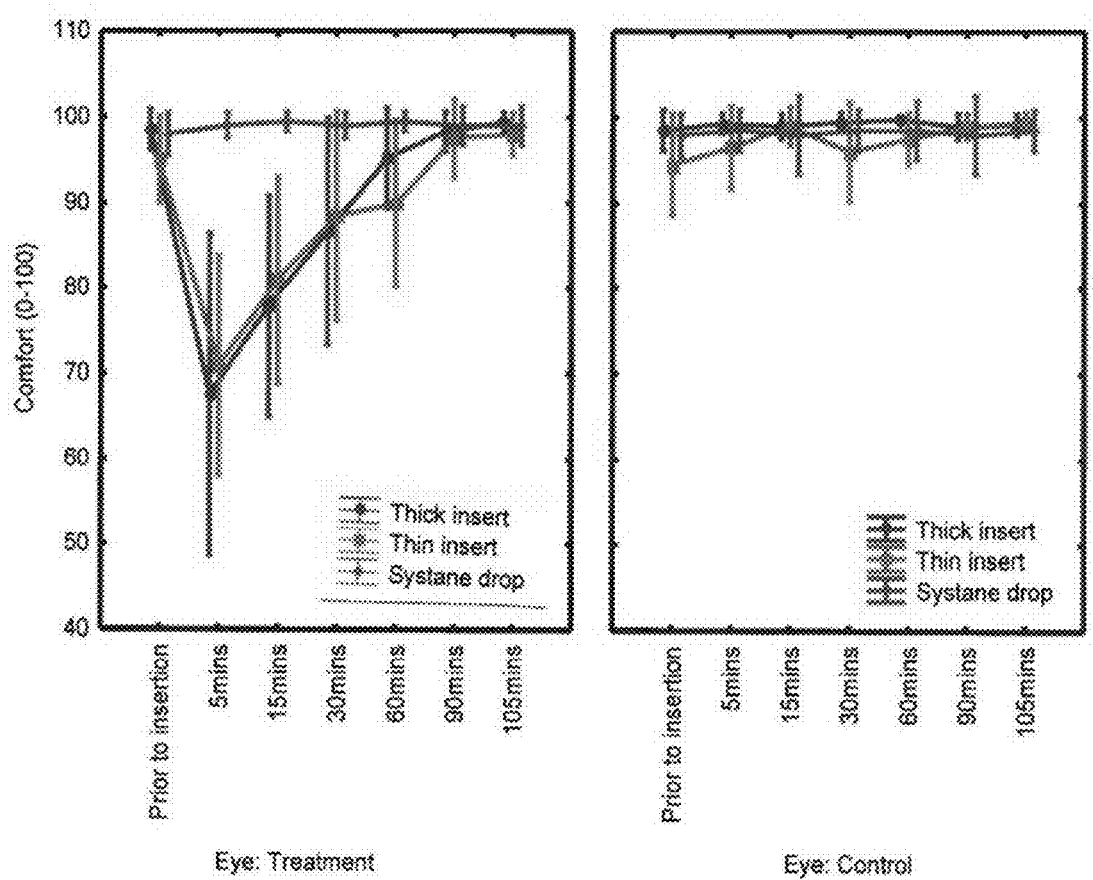
FIG. 11 illustrates the results from the primary outcome measure (comfort rating) of two embodiments (thick insert and thin insert) according to embodiments of the present disclosure.

As seen in FIG. 11, there was a statistically significant difference between the inserts and the drop at the 5 and 15-minute time points, with the drop having statistically significant higher comfort ratings. The two inserts performed similarly in terms of comfort ratings, however there was a statistically significant difference at the 60-minute time point, with the comfort of the thick insert rated higher (90 vs 95, p=0.04).

Secondary Outcome Variable

Results of the Secondary Outcome Variables Were as Follows:

Visual blur—At each of the time points (prior to insertion, 5, 15, 30, 60, 90, and 105 minutes after insertion), participants were asked the following question, "How would you rate the visual blur of your eyes?". Participants responded using a 0 to 100 scale where 0 indicates "Extremely blurry. Unable to see properly" and 100 indicates "Not blurry at all". The results are provided in FIG. 12.

Figure 12:
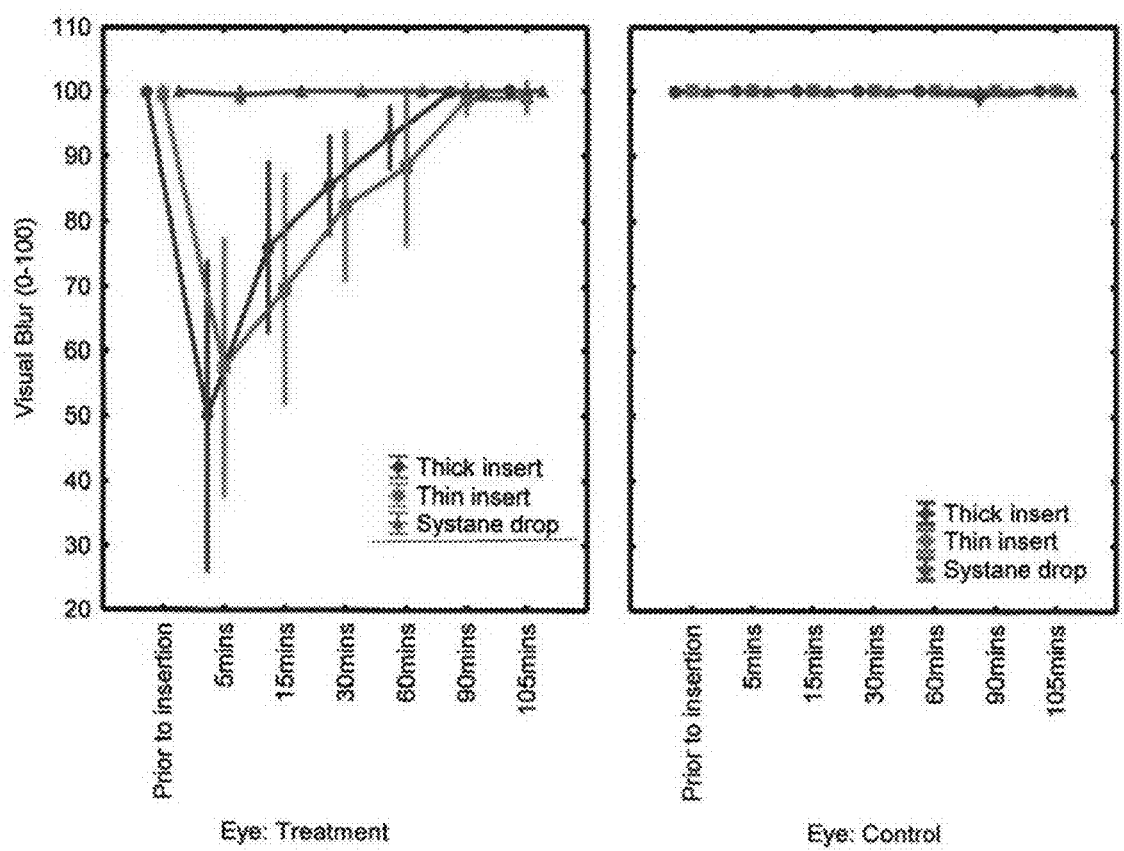
FIG. 12 illustrates the results from a secondary outcome measure (visual blur) of two embodiments (thick insert and thin insert) according to embodiments of the present disclosure.

As seen in FIG. 12, compared to the drops, both inserts caused statistically significantly lower ratings of visual blur at the 5, 15 and 30-minute time points (p<0.01 or p=0.01). Additionally, the thick insert caused a statistically significant lowering of visual blur ratings at the 60-minute time point (93 vs 100, p=0.01), however there was not a statistically significant difference between the thick and thin insert at 60 minutes (88 vs 93, p=0.28).

Ease of insertion by clinicians—Investigators provided an assessment of the ease of insertion of the polymeric eye inserts during at insertion Ease of insertion was assessed using a 0 to 4 scale in 0.5 steps where 0 indicates "Very easy" and 4 indicates "Very difficult".

Results are as follows: Thin insert—1.3±0.5, Thick insert—1.6±0.5. The results show that there were no statistically significant difference in the ease of insertion of the two inserts. Further, Inserts were relatively easy to place in eye even with minimal training.

polymeric eye insert dissolution rate—The degree of dissolution of the polymeric eye inserts were assessed at each time point. At each of the time points (at insertion, 45, 60, 75, 90, and 105 minutes after insertion), Investigators provided an assessment of the degree of dissolution of the polymeric eye inserts. Dissolution grading was done using a 0 to 6 scale, where 0 indicates "No dissolution" and 6 indicates "completely dissolved".

Figure 13:
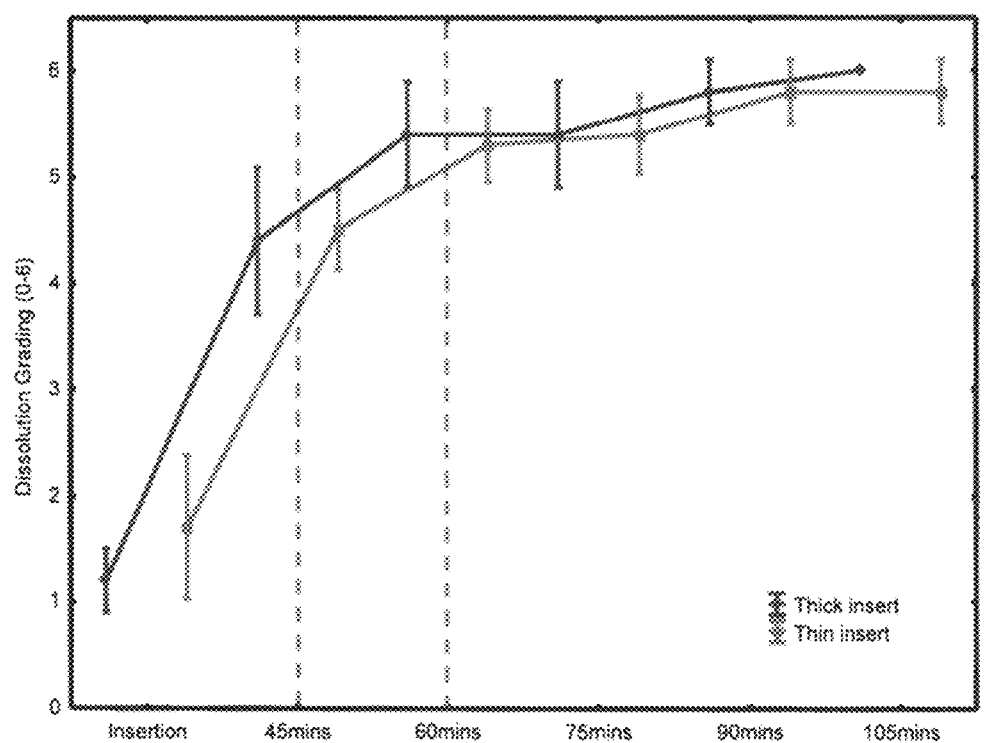
FIG. 13 illustrates the results from the assessment of polymeric eye insert dissolution of embodiments of the present disclosure.

Results are shown in FIG. 13 and indicate that ~90% of the lubricant solid material is dissolved between 60-90 min. Further, the data indicate that there were no statistically significant differences in the dissolution grade of the two inserts.

NITBUT—An assessment of the non-invasive tear breakup time (NITBUT) was performed at insertion and 60 minutes, 90 minutes, and 105 minutes after insertion. Results are presented in FIG. 14.

Figure 14:
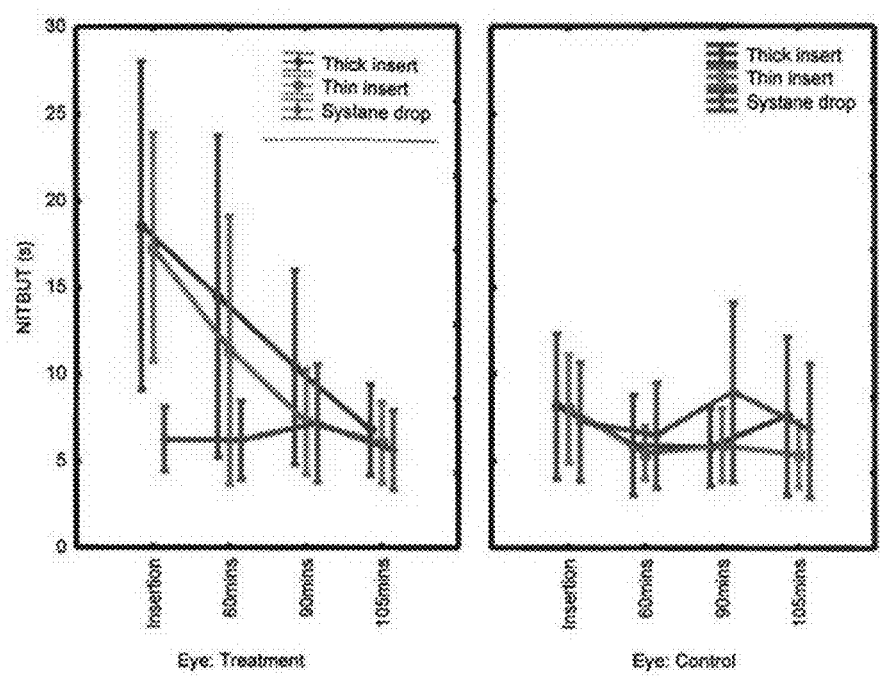
FIG. 14 illustrates the results from a secondary outcome measure (NITBUT) of two embodiments (thick insert and thin insert) according to the present disclosure.

FIG. 14 illustrates that there were statistically significant differences between the treatment eye and the control eye for both inserts at the insertion time point, with the NITBUT of the treatment eye being larger than the control eye (thick insert: 18.52 vs 8.12, p=0.01; thin insert:17.26 vs 7.93, p<0.01). There were also statistically significant differences with the thick insert between treatment and control eyes at the 60 and 90-minute time points (60 mins: 14.47 vs 5.89, p=0.02; 90 mins: 10.36 vs 5.77, p=0.02).

Figure 15:
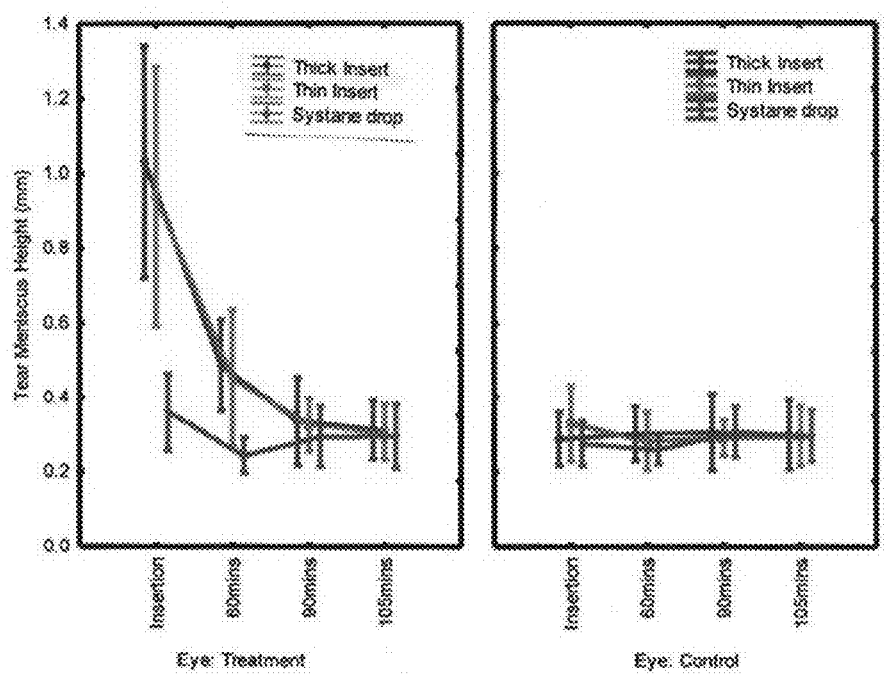
FIG. 15 illustrates the results from a secondary outcome measure (tear meniscus height) of two embodiments (thick insert and thin insert) according to the present disclosure.

Tear meniscus—Investigators provided an assessment of tear film meniscus height during the treatment at time points and 60 minutes, 90 minutes, and 105 minutes after insertion. Results are presented in FIG. 15.

Other Variables

Ocular irritation—At each of the time points (prior to insertion, 5, 15, 30, 60, 90, and 105 minutes after insertion), participants were asked, "How would you rate the feeling of ocular irritation of your eyes?" Participants responded using a 0 to 100 scale where 0 indicates "Intense feeling of ocular irritation" and 100 indicates "No feeling of ocular irritation at all".

Figure 16:
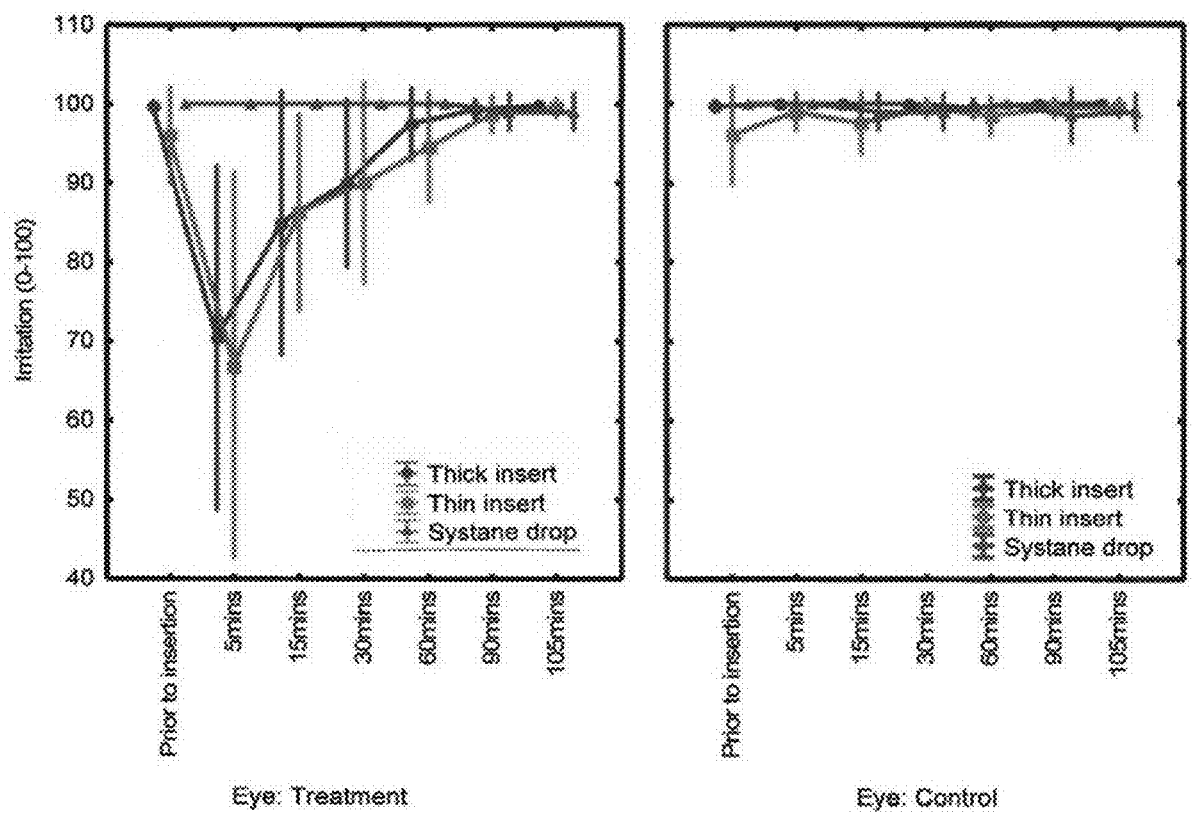
FIG. 16 illustrates results from the ocular irritation question for two embodiments (thick insert and thin insert) according to the present disclosure.

Results are shown in FIG. 16. As seen in FIG. 16, There were statistically significant differences between the treatment eye and the control eye for both inserts at the 5-minute time point, with the ocular irritation rating of the treatment eye being statistically significantly lower (thick insert: 71 vs 100, p=0.01; thin insert: 67 vs 99, p=0.02). There were no statistically significant differences in ocular irritation rating between the two inserts.

Figure 17:
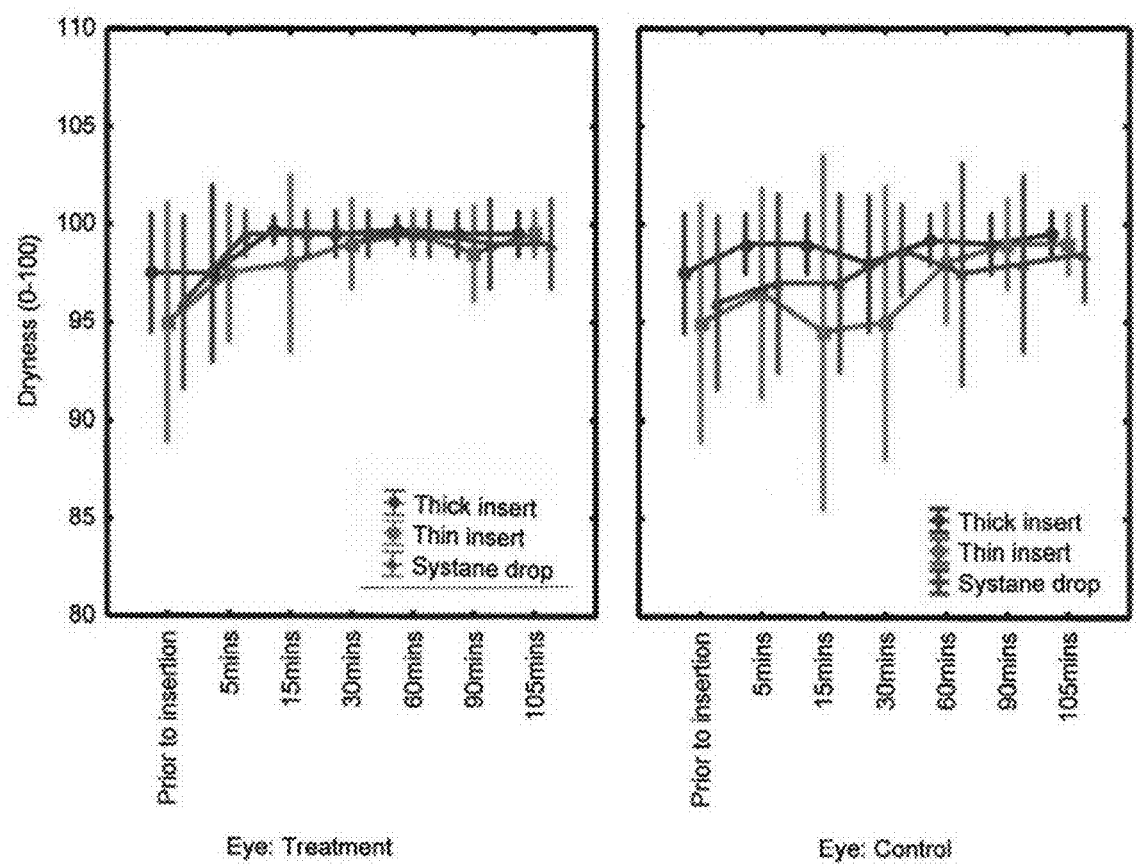
FIG. 17 illustrates results from the ocular dryness question for two embodiments (thick insert and thin insert) according to the present disclosure.

Ocular dryness—At each of the time points (prior to insertion, 5, 15, 30, 60, 90, and 105 minutes after insertion), participants were asked, "How would you rate the dryness of your eyes?" Participants responded using a 0 to 100 scale where 0 indicates "Very dry" and 100 indicates "No dryness at all". Results are shown in FIG. 17. There were no statistically significant differences between the treatment and control eyes in terms of dryness for any treatment. There were also no differences between inserts.

Figure 18:
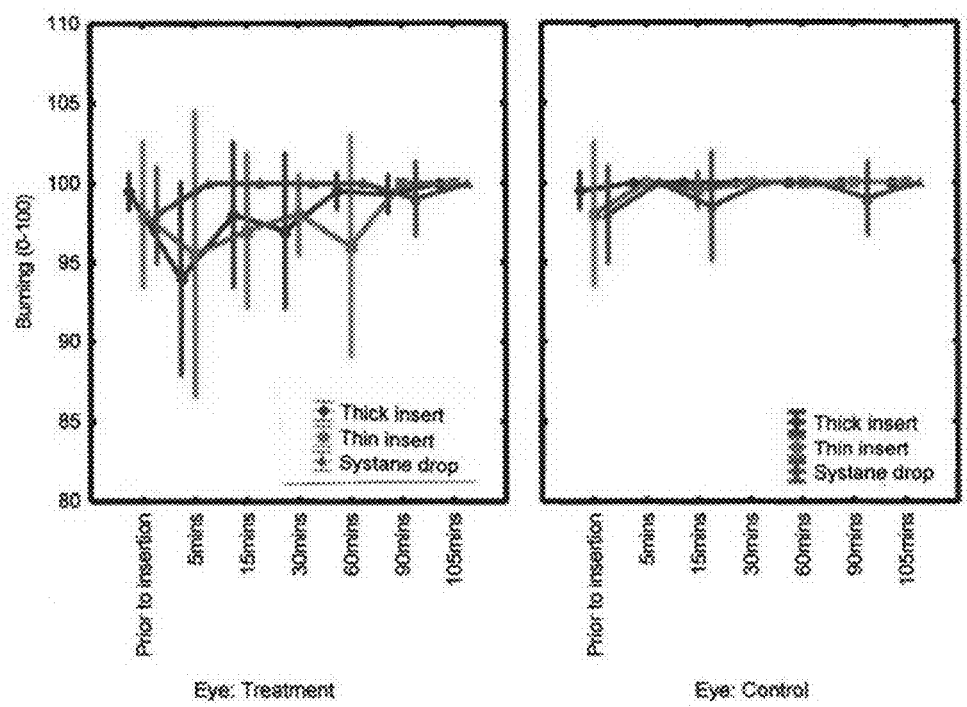
FIG. 18 illustrates results from the ocular burning/stinging question for two embodiments (thick insert and thin insert) according to the present disclosure.

Burning/stinging—At each of the time points (prior to insertion, 5, 15, 30, 60, 90, and 105 minutes after insertion), participants were asked, "How would you rate the burning/stinging sensation of your eyes?" Participants responded using a 0 to 100 scale where 0 indicates "Intense feeling of burning/stinging" and 100 indicates "No burning/stinging at all". Results are presented in FIG. 18. There were no statistically significant differences between the treatment and control eyes in terms of burning/stinging sensation for any treatment. There were also no differences between inserts.

Figure 19:
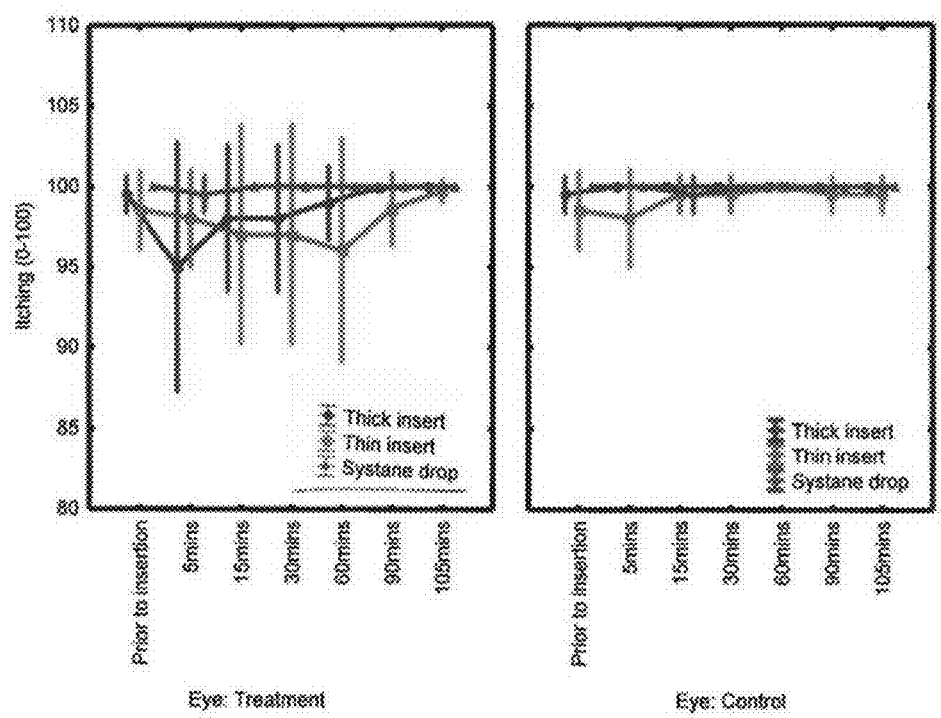
FIG. 19 illustrates results from the ocular itching question for two embodiments (thick insert and thin insert) according to the present disclosure.

Itching—At each of the time points (prior to insertion, 5, 15, 30, 60, 90, and 105 minutes after insertion), participants were asked, "How would you rate the feeling of itchiness of your eyes?" Participants responded using a 0 to 100 scale where 0 indicates "Intense itching" and 100 indicates "No itching at all". Results are presented in FIG. 19. As seen in the results, there were no statistically significant differences between the treatment and control eyes in terms of itching for any treatment. There were also no differences between inserts.

High illumination, high contrast visual acuity—Investigators provided an assessment of high contrast, high illumination visual acuity at screening and during the treatment visits at insertion and 60 and 105 minutes after insertion. There were statistically significant differences between treatment and control eyes at the insertion and 60-minute time points, with participants exhibiting a significant reduction in visual acuity. (Insertion: thick insert: 0.05 vs -0.11, p<0.01; thin insert: 0.07 vs -0.10, p=0.01)(60 mins: thick insert: -0.06 vs -0.1, p=0.03; -0.07 vs -0.10, p=0.02). The difference in visual acuity at 60 minutes equates to approximately 2 letters, which may not be considered clinically relevant. Visual acuity had returned to normal by the end of the treatment visit. There were no statistically significant differences in visual acuity between inserts.

Ocular health—Bulbar and limbal hyperemia (redness) and neovascularization were assessed using a 0-4 scale in 0.1 steps (Efron Scale), with 0 indicating normal and 4 indicating severe. There were no clinically relevant differences for any measure of ocular health.

Summary of Results

Primary clinical outcome of subjective comfort and tolerability was achieved. The inserts were tolerated by the participants and the ocular health for all patients during and post-wear was not negatively affected.

There were no statistically significant differences between SYSTANE ULTRA and the inserts for burning, stinging, itching or dryness in the participants.

Inserts did not negatively impact ocular health.

The in vivo rabbit and clinical comfort study data suggest that the device could be a valuable platform for delivery of ocular lubricants and other topical ocular drugs.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. All of the publications and patent applications and patents cited in this specification are herein incorporated in their entirety by reference.

What is claimed is:

1. A polymeric eye insert, the insert comprising:
   mucoadhesive polymers that are biocompatible with the ocular surface and tear film of the eye and a plasticizer or softener, wherein the mucoadhesive polymers are a combination of HP guar, hyaluronic acid, or sodium hyaluronate and polyvinyl pyrrolidine, wherein the mucoadhesive polymers are present in an amount of from 80% to 90% w/w of the polymeric eye insert, wherein a plasticizer or softener is polyethylene glycol (PEG); and wherein upon insertion of the polymeric eye insert in the cul-de-sac of the eye, the thickness of the tear film increases for at least 30 minutes post-insertion.

2. The polymeric eye insert of claim 1, wherein the plasticizer or softener is present in an amount of from 5% to 25% w/w of the polymeric eye insert.

3. The polymeric eye insert of claim 1, wherein the insert is comprised of approximately 40% w/w HP guar, approximately 10% w/w PVP, approximately 40% w/w sodium hyaluronate, and approximately 10% w/w PEG.

4. The polymeric eye insert of claim 1, further comprising 1-200 ppm menthol.

5. The polymer eye insert of claim 4, comprising 20-100 ppm menthol.

6. The polymeric eye insert of claim 1, wherein the insert comprises one or more pharmaceutically active agents.

7. The polymeric eye insert of claim 5, wherein the one or more pharmaceutically active agents is selected from the group consisting of atropine derivatives which are not nitric oxide donors, travoprost co-drug with nitric oxide, lubricants, steroids, antibiotics, nonsteroidal anti-inflammatory drugs, anti-histamines, anti-virals, anti-bacterials, vasoconstrictors, and prostaglandin analogs.

8. The polymeric eye insert of claim 1, wherein the tear film thickness does not return to pre-insertion thickness until approximately two hours after insertion.

9. The polymeric eye insert of claim 1, wherein upon insertion in the cul-de-sac of the eye, the thickness of the tear film increases up to at least two hours post-insertion.

10. The polymeric eye insert of claim 1, wherein the insert shape is a film.

11. The polymeric eye insert of claim 1, wherein said HP guar has a weight average molecular weight of 2 to 4 million Daltons and said sodium hyaluronate has a weight average molecular weight of 0.1 to 2 million Daltons.

12. A method of treating an ocular disorder, which comprises applying the polymeric eye insert of claim 1 to the cul-de-sac of the eye, wherein said ocular disorder is selected from the group consisting of dry eye, eye redness, myopia, glaucoma, allergy, and inflammation.

* * * * *